United States Patent [19]
Kaplan et al.

[11] Patent Number: 5,932,119
[45] Date of Patent: Aug. 3, 1999

[54] LASER MARKING SYSTEM

[75] Inventors: George R. Kaplan, Rye Brook, N.Y.;
Avigdor Shachrai, Netanya, Israel;
Oded Anner, Kfar-Saba, Israel; Leonid Gurvich, Rishon Lezion, Israel

[73] Assignee: Lazare Kaplan International, Inc., New York, N.Y.

[21] Appl. No.: 08/690,309

[22] Filed: Jul. 30, 1996

Related U.S. Application Data

[60] Provisional application No. 60/009,638, Jan. 5, 1996.
[51] Int. Cl.$^6$ ................................... B23K 26/00
[52] U.S. Cl. ............................ 219/121.68; 219/121.83
[58] Field of Search ................ 219/121.68, 121.69, 219/121.62, 121.82, 121.83; 364/474.08; 372/13

[56] References Cited

U.S. PATENT DOCUMENTS

| | | |
|---|---|---|
| 671,830 | 4/1901 | Loesser . |
| 671,831 | 4/1901 | Loesser . |
| 694,215 | 2/1902 | Stuurman . |
| 732,118 | 6/1903 | Schenck . |
| 732,119 | 6/1903 | Schenck . |

(List continued on next page.)

FOREIGN PATENT DOCUMENTS

| | | |
|---|---|---|
| 643142 | 10/1927 | France . |
| 2496888 | 12/1980 | France . |
| 133023 | 12/1900 | Germany . |
| 130138 | 5/1901 | Germany . |
| 48-100291 | 11/1973 | Japan . |
| 50134362 | 5/1977 | Japan . |
| 57-137091 | 8/1982 | Japan . |
| 1-58544 | 3/1989 | Japan . |
| 3-146285 | 6/1991 | Japan ................................ 219/121.62 |
| 4-08489 | 1/1992 | Japan . |
| 6170571 | 6/1994 | Japan . |
| 7-077989 | 8/1995 | Japan . |
| 122470 | 1/1919 | United Kingdom . |
| 1057127 | 10/1963 | United Kingdom . |
| 1059249 | 12/1965 | United Kingdom . |
| 1094367 | 12/1965 | United Kingdom . |
| 1254120 | 12/1968 | United Kingdom . |
| 1292981 | 1/1969 | United Kingdom . |
| 1265241 | 2/1970 | United Kingdom . |
| 1326775 | 12/1970 | United Kingdom . |
| 1324903 | 4/1971 | United Kingdom . |
| 1377131 | 2/1972 | United Kingdom . |
| 1384813 | 2/1972 | United Kingdom . |
| 1405487 | 9/1972 | United Kingdom . |
| 1416568 | 10/1973 | United Kingdom . |
| 1446806 | 4/1974 | United Kingdom . |
| 2010474 | 1/1979 | United Kingdom . |
| 2052369 | 6/1980 | United Kingdom . |
| 2140555 | 5/1984 | United Kingdom . |

*Primary Examiner*—Geoffrey S. Evans
*Attorney, Agent, or Firm*—Milde, Hoffberg & Macklin, LLP

[57] ABSTRACT

A laser energy microinscribing system, including a semiconductor excited Q-switched solid state laser energy source; a cut gemstone mounting system, allowing optical access to a mounted workpiece; an optical system for focusing laser energy from the laser energy source onto a cut gemstone; a displaceable stage for moving said gemstone mounting system with respect to said optical system so that the focused laser energy is presented to desired positions on the gemstone, having a control input; an imaging system for viewing the gemstone from a plurality of vantage points; and a rigid frame supporting the laser, the optical system and the stage in fixed relation, to resist differential movements of the laser, the optical system and the stage and increase immunity to vibrational misalignments. The laser energy source is preferably a semiconductor diode excited Q-switched Nd:YLF laser with a harmonic converter having an output of about 530 nm. The system may further include an input for receiving marking instructions; a processor for controlling the displaceable stage based on the marking instructions and the imaging system, to selectively generate a marking based on the instructions and a predetermined program; and a storage system for electronically storing information relating to images of a plurality of workpieces. A secure certificate of authenticity of a marked workpiece is also provided.

88 Claims, 16 Drawing Sheets

U.S. PATENT DOCUMENTS

| | | |
|---|---|---|
| 2,351,932 | 6/1944 | Deckel et al. . |
| 3,407,364 | 10/1968 | Turner . |
| 3,414,354 | 12/1968 | Siegler, Jr. . |
| 3,440,388 | 4/1969 | Otstot et al. . |
| 3,527,198 | 9/1970 | Taksoka ............................... 125/30.01 |
| 3,537,198 | 11/1970 | Barrett . |
| 3,622,739 | 11/1971 | Steffen ................................. 219/121.7 |
| 3,700,850 | 10/1972 | Lumley et al. .................... 219/121.69 |
| 3,775,586 | 11/1973 | Flint et al. ......................... 219/121.63 |
| 3,989,379 | 11/1976 | Eickhorst . |
| 4,048,515 | 9/1977 | Liu . |
| 4,059,471 | 11/1977 | Haigh . |
| 4,121,003 | 10/1978 | Williams . |
| 4,178,404 | 12/1979 | Allen et al. . |
| 4,199,615 | 4/1980 | Wacks et al. . |
| 4,247,318 | 1/1981 | Lee et al. . |
| 4,259,011 | 3/1981 | Crumm et al. . |
| 4,392,476 | 7/1983 | Gresser et al. ....................... 219/121.6 |
| 4,394,580 | 7/1983 | Gielisse . |
| 4,397,556 | 8/1983 | Muller . |
| 4,401,876 | 8/1983 | Cooper ............................... 219/121.69 |
| 4,405,829 | 9/1983 | Rivest et al. . |
| 4,414,967 | 11/1983 | Shapiro . |
| 4,463,250 | 7/1984 | McNeight et al. . |
| 4,467,172 | 8/1984 | Ehrenwald et al. ............... 219/121.68 |
| 4,494,381 | 1/1985 | Lessard . |
| 4,507,349 | 3/1985 | Fromson et al. . |
| 4,507,744 | 3/1985 | McFiggans et al. . |
| 4,514,085 | 4/1985 | Kaye . |
| 4,620,284 | 10/1986 | Schnell et al. . |
| 4,630,201 | 12/1986 | White . |
| 4,637,051 | 1/1987 | Clark . |
| 4,693,377 | 9/1987 | Gerrard et al. . |
| 4,761,786 | 8/1988 | Baer ......................................... 372/13 |
| 4,799,786 | 1/1989 | Gerrard . |
| 4,812,965 | 3/1989 | Taylor . |
| 4,814,589 | 3/1989 | Storch et al. . |
| 4,816,655 | 3/1989 | Musyck et al. . |
| 4,847,850 | 7/1989 | Kafka et al. ............................... 372/13 |
| 4,853,961 | 8/1989 | Pastor . |
| 4,875,771 | 10/1989 | Bowley et al. . |
| 4,913,858 | 4/1990 | Miekka et al. . |
| 4,981,370 | 1/1991 | Dziewit et al. . |
| 5,018,767 | 5/1991 | Wicker . |
| 5,073,935 | 12/1991 | Pastor . |
| 5,099,101 | 3/1992 | Millerick et al. ................... 219/121.82 |
| 5,113,445 | 5/1992 | Wang . |
| 5,142,577 | 8/1992 | Pastor . |
| 5,149,938 | 9/1992 | Winston et al. .................... 219/121.69 |
| 5,163,091 | 11/1992 | Graziano et al. . |
| 5,166,978 | 11/1992 | Quisquater . |
| 5,173,584 | 12/1992 | Kahlert et al. ...................... 219/121.83 |
| 5,190,024 | 3/1993 | Senanayake . |
| 5,191,613 | 3/1993 | Graziano et al. . |
| 5,193,853 | 3/1993 | Wicker . |
| 5,225,650 | 7/1993 | Babel et al. ......................... 219/121.69 |
| 5,243,641 | 9/1993 | Evans et al. . |
| 5,263,085 | 11/1993 | Shamir . |
| 5,283,422 | 2/1994 | Storch et al. . |
| 5,337,362 | 8/1994 | Gormish et al. . |
| 5,367,148 | 11/1994 | Storch et al. . |
| 5,367,319 | 11/1994 | Graham . |
| 5,370,763 | 12/1994 | Curiel . |
| 5,375,170 | 12/1994 | Shamir . |
| 5,380,047 | 1/1995 | Molee et al. . |
| 5,384,846 | 1/1995 | Berson et al. . |
| 5,388,158 | 2/1995 | Berson . |
| 5,393,099 | 2/1995 | D'Amato . |
| 5,410,125 | 4/1995 | Winston et al. .................... 219/121.69 |
| 5,420,924 | 5/1995 | Berson et al. . |
| 5,422,954 | 6/1995 | Berson . |
| 5,426,700 | 6/1995 | Berson . |
| 5,464,690 | 11/1995 | Boswell . |
| 5,499,294 | 3/1996 | Friedman ................................. 380/10 |
| 5,614,114 | 3/1997 | Owen ................................. 219/121.71 |

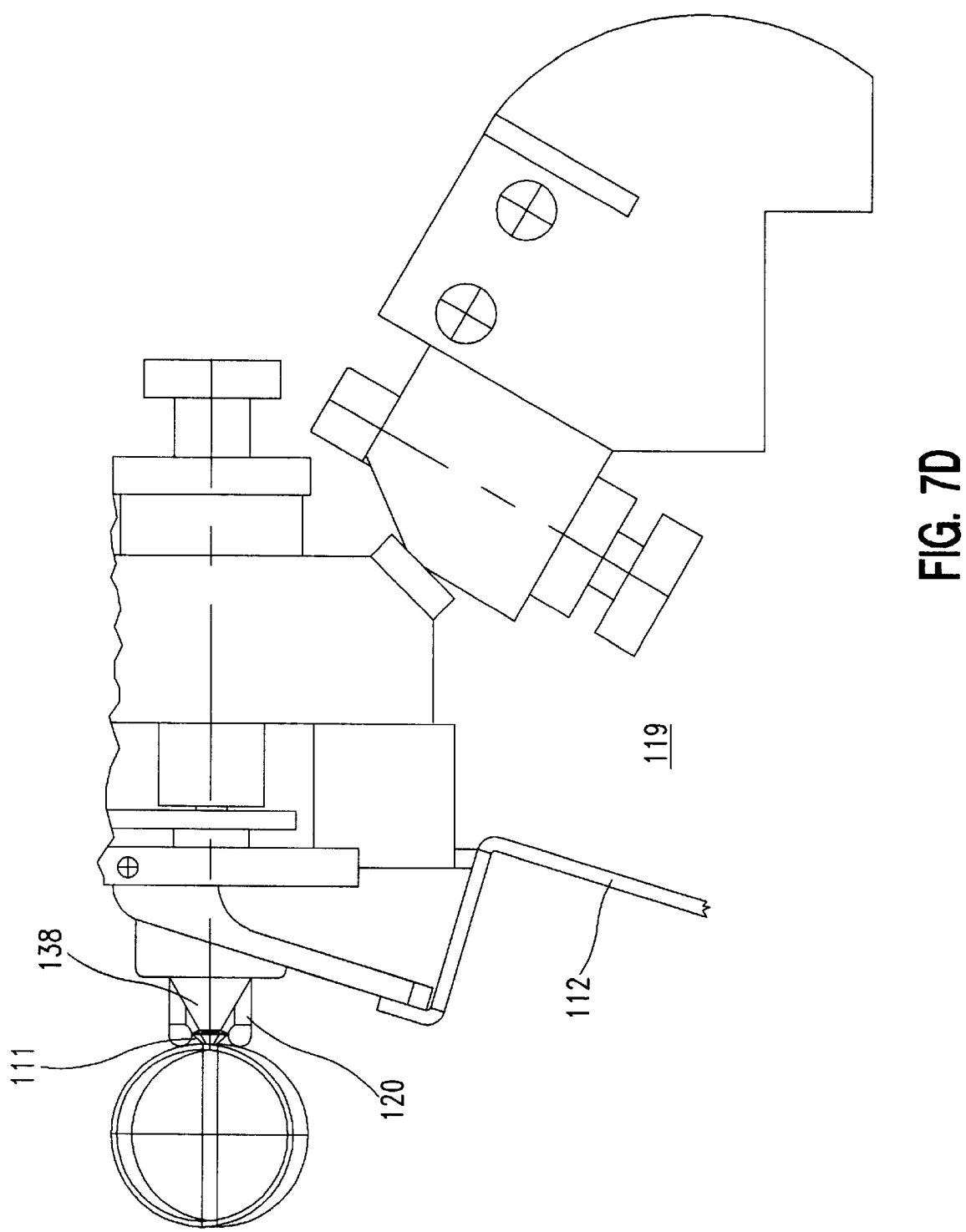

LASER MARKING SYSTEM

This application claims benefit of Provisional Application No. 60/009,638 filed Jan. 5, 1996.

FIELD OF THE INVENTION

The present invention relates to the field of inscribing indicia on a surface of gemstones, and more particularly to a system employing a Q-switched pulse laser for forming markings on a portion of a gemstone.

BACKGROUND OF THE INVENTION

A known system, as described in U.S. Pat. No. 4,392,476, incorporated herein by reference, for inscribing diamonds includes a Nd:YAG (1.06 μm, frequency doubled) Q-switched laser which marks diamonds by graphitizing the surface at a laser focal point. The beam position is computer controlled to create overlapping treated regions. The accuracy of known embodiments of this system are limited by vibration and laser steering system accuracy.

U.S. Pat. No. 4,467,172, incorporated herein by reference, describes a laser beam diamond inscribing system, which provides a Q-switched flashlamp pumped YAG laser (1.06 μm, frequency doubled) with the diamond mounted on a computer-controlled positioning table for inscribing alphanumeric characters. See also, U.S. Pat. Nos. 2,351,932, 3,407,364, 3,527,198, 3,622,739, 3,775,586 and 4,048,515, and foreign patents JP 00-48,489 and JP 00-77,989.

U.S. Pat. Nos. 5,410,125 and 5,149,938 describe systems which produce a gemstone marking by employing an excimer laser (193 nm) with a masked marking image. Thus, repositioning to form complete characters or graphics is unnecessary. The diamond selectively absorbs the excimer laser radiation and undergoes a partial allotropic transformation without losing its diamond crystal lattice configuration. See also, U.S. Pat. Nos. 3,527,198 and 4,401,876. U.S. Pat. No. 5,410,125 is a continuation-in-part of Ser. No. 595,861, issued as U.S. Pat. No. 5,149,938.

Gemstone News, Nov. 2, 1995 "Serial Numbers are Laser Inscribed", and Jeweler's Keystone-Circular, June 1996, pp. 76 relate to gemstones inscribed with serial numbers or markings.

U.S. Pat. No. 3,537,198 relates to a method of working diamonds using laser energy. U.S. Pat. No. 5,190,024, relates to a diamond sawing process. A laser can be used both to mark and saw the diamond in one operation. See also, U.S. Pat. Nos. 671,830, 671,831, 694,215, 732,118, 732,119, 3,527,198 and 4,392,476, as well as Foreign Reference GB 122,470.

U.S. Pat. No. 4,401,876 relates to a system for kerfing a gemstone such as a diamond, employing a high energy, high pulse rate, low order mode, laser beam. See also, U.S. Pat. Nos. 3,440,388, 3,527,198 and 3,700,850, as well as foreign references BE 877,326, DE 130,138, DE 133,023, GB 1,057,127, GB 1,059,249, GB 1,094,367, GB 1,254,120, GB 1,265,241, GB 1,292,981, GB 1,324,903, GB 1,326,775, GB 1,377,131, GB 1,405,487, GB 1,446,806, GB 2,052,369, Laser Institute of America, "Guide for Material Processing by Lasers" 1978; "Industrial Diamond Review", Mar. 1980, pp. 90 and 91; "Laser Application Notes", 1(1) (Feb. 1979); "New Hyperyag", on Model DLPY 4-System 2000 Yag Laser; and "Diamonds": N.A.G. Press LTD, Chapter Eleven, pp. 235, 239–242.

U.S. Pat. No. 4,799,786, incorporated herein by reference, relates to a method of diamond identification provides a method for the identification of diamonds in which a sample to be identified is placed in a beam of monochromatic laser radiation of pre-determined wavelength. The scattered Raman radiation emitted from the sample is passed through a filter adapted to pass only scattered Raman radiation of frequency characteristic of a diamond. The filtered radiation is then detected by the human eye or a photocell device. See also, U.S. Pat. Nos. 4,397,556 and 4,693,377, and foreign patent GB 2,140,555, Melles Griot, Optics Guide 3, 1985, pp. 1, 333, 350, 351; and Solin et al., Physical Review B, 1(4):1687–1698 (Feb. 15, 1970).

U.S. Pat. No. 4,875,771, incorporated herein by reference, relates to a method for assessing diamond quality, by assessing diamonds with a laser Raman spectrometer. The system is initially calibrated by use of diamonds with known quality characteristics, the characteristics having been assessed, for example, by a conventional subjective procedure. Diamonds of unknown quality characteristics are then placed in the spectrometer and irradiated with laser radiation. The intensity of the scattered Raman signal from the diamond is monitored for one or more orientations of the diamond, the resultant signal being a characteristic of the diamond and believed to indicate a quality level of the diamond. See also, U.S. Pat. Nos. 3,414,354, 3,989,379, 4,259,011, 4,394,580, 4,397,556 and 4,620,284, and foreign patents FR 643,142, FR 2,496,888, JP 01-58,544, GB 1,384,813, GB 1,416,568, GB 2,010,474, GB 0,041,348 and GB 2,140,555, S. A. Solin and K. A. Ramdas, Raman Spectrum of Diamond, Physical Review vol. 1(4), pp. 1687–1698.

The aforementioned documents detail components, methods and systems which may be applied in the construction and operation of the present invention.

SUMMARY OF THE INVENTION

The present invention provides a system having a pulse laser, such as a Q-switched laser diode excited Nd:YLF laser, which produces a series of ablated or graphitized spots on the surface of a workpiece, such as a diamond gemstone. The workpiece is mounted on a translatable stage, for focusing and positioning of the beam.

The translatable stage is controlled by a computer to produce a complex marking pattern. This computer may also be used for process control and imaging, as well as other functions.

The process according to the present invention typically achieves a positioning accuracy of about ±1 micron. The laser and translatable mounting stage are compact and are preferably rigidly mounted on a common platform, allowing sufficient common mode vibration immunity so that only standard vibration damping need be employed rather than extraordinary damping. Therefore, simple and small passive vibration isolation mounts for the platform or chassis are employed, rather than requiring active vibration suppression systems as in known systems.

Optical feedback of the process is possible through one or more video cameras, e.g., 2 CCD imagers provided at right angles, which are provided with a field of view including the focal point of the laser. The correct positioning of the gemstone may thus be assured by correct alignment of the imagers on the workpiece. One imager is directed at the work surface along the axis of the laser, and has a focal plane including the focal point of the laser. Optical feedback through the imagers may also be used to monitor the progress of the marking process, and therefore may be used to adjust workpiece positioning as well as inscription speed, number, intensity and/or rate of pulses at a given location, as well as to verify progress of the marking process. One imager is directed to view a top portion of the workpiece, e.g., directed perpendicular to the table surface of a diamond, allowing identification of a girdle profile, while the second imager is directed to view a side portion of the workpiece, e.g., a profile, and also providing a direct view of the girdle of a gemstone. Thus, the second imager may be used to view the marking process in real time.

The optical feedback system also allows the operator to design an inscription, locate the inscription on the workpiece, verify the marking process and archive or store an image of the workpiece and formed markings.

The markings themselves may have an invariant inscription, a fully automated inscription, e.g., a serial number, a semiautomated inscription, e.g., having a fixed and variable portion, or a fully custom inscription, including graphics.

According to one embodiment, an inscription for a gemstone is defined in relation to a bar code which accompanies the packaging for the gemstone or a preprinted sheet. A bar code reader is provided for the operator to input the bar codes into a computer, without having to retype the data and with lower risk of error. Thus, an inscription may include a fixed portion, e.g., a logo or trademark, a semivariable portion, e.g., a gem rating or grading, and a hypervariable portion, e.g., a serial number. In this case, for example, a logo or trademark is preprogrammed, and inscribed on every workpiece in a series. The gem rating or grading can be scanned as a bar code, printed on a sheet associated with that gemstone, such as a receipt or label. The serial number may be automatically determined, and for example, printed on a receipt or label, and employed as a unique identifier to be applied to the stone. The inscribed characters need not be limited to alphanumeric symbols, and in fact may be fonts in any language, line-drawing characters, custom characters or pictorial representations.

The workpiece may be associated with data, stored in a medium physically associated with the workpiece or in a remote medium accessible through use of an identification of the workpiece. For example, the associated memory is a nonvolatile memory, such as a battery-backed random access memory, an electrically erasable read only memory, a ferroelectric memory, or other storage media such as magnetic stripes, rotating magnetic media, optical memories, and printed matter.

A vanity inscription may be provided on the workpiece as a custom or semicustom inscription, which may be provided as computer text, graphics or a computer-scanned image. The marking system may be employed to mark portions of a gemstone other than the girdle, for example the table. Therefore, in the case of such vanity inscriptions, the intent may be to provide a visible inscription, to enhance the sentimental value of the workpiece, rather than to provide an unobtrusive microscopic identification or authentication marking.

In many instances, it is desired that each inscribed workpiece be separately identifiable. This may be by way of a unique marking on the stone or a unique combination of marking and easily identified characteristics of the workpiece, such as weight, shape, type, etc. In one embodiment, the markings themselves form a code, such as an alphanumeric or bar code, which may be electronically or automatically read or ascertained from an examination of the workpiece.

An image of the marked workpiece may be formed or printed on a certificate which accompanies the workpiece, allowing verification that the workpiece corresponds to the certificate by studying the image in comparison with the actual workpiece. The image advantageously includes all or a portion of the marking, as well as identifiable features of the workpiece, such as landmarks, edges, facets, etc. Thus, the image may be used as a "fingerprint" identification of the workpiece. The image on the certificate may be formed photographically or electronically. Thus, the image as stored need not be formed through the CCD images or the marking system, and may be produced as a separate step.

Advantageously, an image of a completed marking or a bitmap of an inscription program is stored in a database, and therefore is available for comparison and later authentication of a workpiece, and to prevent inadvertent or undesired duplicate markings. The storage may be electronic or photographic, and thus the database may reside on magnetic or magnetooptical media, microfilm, paper or film, holographic crystals, magnetic or optical tape, or other known media.

In accordance with one aspect of the invention, a duplicate-prevention function is provided integral to the marking device which may not be overridden by a user, e.g., to prevent inadvertent or intentional misuse of the system. In this case, the laser system may include a lockout circuit which prevents activation of the laser control and positioning systems under unauthorized circumstances. Such a lockout may be provided in the power supply or other critical subsystem of the device.

Based on the use of the marking system, a report may be generated by the computer/controller. Because the inscription is a raster ablated image, such report may advantageously include either the programmed inscription as a graphic printout or an image received from the optical feedback imaging system, e.g., the video camera. As stated above, the report may also include or be associated with a certificate of authenticity, e.g., including a facsimile of the workpiece image including the marking. A known image authentication scheme is disclosed in U.S. Pat. No. 5,499, 294, incorporated herein by reference.

The entire workpiece is generally mounted on a translatable stage, allowing precise positioning. Thus, for compact designs, the holder may accommodate workpieces of less than about 30 mm in a largest dimension, although the stage is capable of accurate positioning over a larger distance. The stage is generally translatable along three axes, X, Y, and Z in a Cartesian coordinate system, but may also include other axes, e.g., rotational axes. For example, a brilliant cut diamond is radially symmetric. Therefore, where an inscription or marking is desired around the diamond girdle, the diamond may be held in focus by adjusting a Z axial displacement and an inscription defined by translation along the X and Y axes during laser pulsing. Alternately, the diamond may be initially positioned appropriately along the X, Y and Z axes, and rotated about an axis and translated sequentially along a Y axis to define the inscription. In this case, the Z axis and possibly X axis may also be used to retain focus condition. Where X, Y and Z axes are employed for automated control, a manual rotational control is preferably provided with detents at regular intervals.

The positioning system, for moving the workpiece in relation to the laser focal point may also include or be formed from beam steering systems, such as mirrors, electrooptical elements, spatial light modulators, such as the Texas Instruments Digital Mirror Device ("DMD", also known as Digital Light Processor, "DLP"), holographic or diffractive elements, or other optical systems. However, a translatable stage is a preferred means for directing the focused laser energy onto a desired portion of the workpiece.

The workpiece generally sits in a holder which detachably mounts to the translatable stage. Thus, a workpiece may be suitably mounted in a holder outside the apparatus while another workpiece is being inscribed. These holders may also increase the versatility of the device by providing adaptation to workpieces or various sizes and shapes. For example, round, oval, heart, marquis and other cut diamonds may each be provided with separately optimized holders; further, diamonds of various size ranges may be accommodated by differing holders, as necessary.

According to another embodiment, a mounted workpiece, e.g., a diamond in a setting, may be inscribed on portions which are not obscured. For example, in a pronged setting, a portion of the girdle may be exposed, and thus may be available for marking. In this case, a multi-articulated holder or set of holders may be provided to properly position the workpiece within the inscribing chamber of the device. Holders may be provided to accommodate mounted gems in rings, earrings, pendants, and possibly bracelets, brooches, and other common forms.

The computerized control system provides a user interface making the various functionality accessible to users, and may further limit use and operation to safe and/or desired activities. Therefore, the computerized control system may be programmed to limit activities which would damage the workpiece, circumvent security or authentication procedures, or otherwise be undesired. The computerized control system may therefore require user authentication, employ video pattern recognition of the workpiece, especially markings on the workpiece, and control operation of the laser system to avoid damage to the system components or the particular workpiece. The system may also acquire an image, fingerprint, retinal image or other secure identification of the operator.

The system may also include a diamond or gemstone analysis system for describing the quality and/or characteristics of the workpiece. This analysis may be employed by the system in order to optimize the marking process, generate data to be marked on the workpiece, and/or to store data identifying the workpiece in relation to the marking. This system may operate automatically or semiautomatically. It is noted that, where gemstone classification automation is employed, a failsafe classification scheme will generally be employed which provides a manual classification or preclassification first. Thus, the risk of mismarking or misclassification will be reduced by the redundancy. The characteristics of the workpiece may be used to control parameters of the marking process.

Where a diamond having a polished girdle is to be marked, a single pass inscription is generally sufficient, and an automated optical feedback system may reliably control operation. However, the optical absorption of a smooth girdle on a diamond is low, so that a dye or ink coating is required to be placed on the surface, to ensure absorption of the laser energy. Where the girdle is rough, multiple passes of the inscription device may be necessary to generate a desired marking. The optical absorption of a rough girdle is generally high enough to dispense with the need for optically absorptive dyes or inks. While the execution of retries may be automated, user control may be desirable, and such control is possible through use of the video cameras which are directed at the workpiece, which display a real time image on a computer monitor.

An optically absorptive dye or ink may be manually applied to the workpiece, such as by a marking pen, or the application process may be automated by applying the dye to a workpiece surface to be marked, such as with a porous marking tip. Advantageously, these inks or optically absorptive dyes remain on the surface of the workpiece, and would not be expected to penetrate. In general, a dye is selected which may be easily removed after marking by use of a solvent, such as alcohol. The dye may be removed manually or through an automated process, such as wiping with a solvent saturated pad.

In another embodiment, relief inscriptions are possible by modulating the laser pulses or selectively multiply ablating or graphitizing the workpiece at desired positions. Such relief markings are generally not necessary for simple alphanumeric or digital code inscription, but may be useful for logos, pictorial works, antialiasing of raster images, binary or Fresnel-type optics, diffraction optic effects, anti-piracy or anti-copying provisions, or in other circumstances.

In systems provided with two video cameras, video profiling of the workpiece is possible, which may be used to determine an optimal position of the workpiece for marking without requiring focus checking at each location. The dual cameras also allow positioning and viewing on the same video screen, wherein the camera views are each provided as separate image windows. The cameras are useful for determining an appropriate marking location, ensuring laser beam focus, aligning the stone, and monitoring progress of the marking process.

The computerized control system allows versatility in the design, selection and implementation of graphic and font inscription. In a preferred embodiment, Borland fonts are employed. However, other fonts or combinations of fonts may also be employed, for example, Borland, postscript, TrueType, plotter, or other type fonts or typefaces may be employed. Further, the marking system may be set up to respond to Adobe Postscript, Microsoft Windows GDI, Macintosh QuickDraw, HP-GL, or other graphics standards.

A preferred laser system is a self-standing diode laser pumped Q-switched Nd:YLF laser with an internal frequency doubler. Such a system avoids the requirements of a relatively large YAG laser with large power supply and strict environmental control, an external frequency doubler, a water cooling system, large size and weight, inherent instability, and long optical path.

A green filter is provided on the output of the laser to selectively filter laser diode emissions, while allowing the green (530–540 nm) laser emissions to pass. The laser diode illumination is undesirable because it saturates the image on the vertical (Z-axis) camera screen in the laser spot area and prevents convenient viewing of the girdle and inscription.

The preferred translatable stage arrangement overcomes a typically limited range of optical movement of laser steering systems, requiring inscription operations in multiple segments, and provides good absolute positioning repeatability. However, according to some embodiments of the invention, other types of beam positioning apparatus may be employed, such as beam steering systems.

A marking may be provided on the stone for a number of reasons. First, it may be desirable to identify a stone if it is lost or mixed with other stones. The marking may also be used to identify source or origin. In this case, the marking may be taken at face value.

In some instances, however, a risk of forgery or simulation requires further security measures. Therefore, it may be desired to ensure that the stone was marked by an indicated entity, or that the stone corresponds to the marking applied thereto. This requires one of at least two possible schemes.

First, that a characteristic of the stone be unique and very difficult to simulate. For example, certain dimensions or ratios of the gemstone are the subject of somewhat random variations, and thus have a somewhat uncontrolled range of values. Natural flaws and other characteristics are also generally random in nature, and thus also difficult to simulate. It is therefore unlikely that one stone will correspond to another stone, and it is unlikely that another stone can be made to identically correspond to the determined dimensions and ratios through manipulations.

According to one aspect of the invention, therefore, these difficult to reproduce characteristics are used as an integrity check for an encoded message. These characteristics may be measured or recorded, and stored. Advantageously, these measurements and characteristics may be derived from an image of the stone captured in conjunction with the marking process. In fact, by storing such images and providing a pointer to the image, e.g., a serial number, the measurements or characteristics to be compared need not be determined in advance. Therefore, according to such a scheme, the stone need only include a pointer to a record of a database containing the data relating to the stone to be authenticated. This allows information relating to characteristics of the stone, which may be difficult to repeatably determine or somewhat subjective, to be preserved in conjunction with the stone or an identification of the stone. As stated above, an image of the stone on a certificate of authenticity may be used to verify that the stone is authentic, while providing a tangible record of the identification of the stone.

Another scheme relies instead on the difficulty in identically copying an inscription, including subtle factors and interactions of the laser marking beam with the stone itself Thus, the marking itself is self-authenticating. An attempt to copy the marking will likely fail because of the technological limitations on the laser marking techniques, and/or insufficient information to determine all of the encoding information.

Thus, to authenticate a stone, either the markings alone or the markings in conjunction with the characteristics or physical properties of the stone are analyzed. In one scheme, the markings inscribed on the stone include information which correlates with characteristics of the stone which are hard to duplicate, and which recur with rarity, allowing self-authentication. In other schemes, the marking inscribed on the stone identifies a database record stored in a repository, thus requiring communication with the repository to obtain the authentication information. The hand cutting process for gemstones makes it is difficult or impossible to identically duplicate all measurable aspects of a stone, especially in conjunction with other physical characteristics, such as natural flaws. Such physical properties may include, for example, the girdle width at predetermined locations. The location may be identified, e.g., by an inscribed marking or by an offset from a marking which is not apparent from an examination of the stone alone. For any given gemstone, one or more such locations may be stored, thus increasing the difficulty in simulating the measurement. Further, such measurements are generally easy to obtain or determine from the imaging system of the inscribing system.

Sophisticated techniques, such as Raman scattering analysis, are known which may provide unique information about a particular natural crystal structure. While the preferred system does not employ Raman scattering analysis, such analysis may be used in conjunction with embodiments of the invention.

According to a preferred embodiment, the authenticity of a stone is determined may be determined by use of a jeweler's loupe to compare the actual stone to an image of the stone, such as may be provided on or in conjunction with a certificate of authenticity. Because each stone has varying characteristics, including the marking, details of the cut, and the relationship of the marking to the landmarks of the stone, the image serves as a fingerprint, making each stone essentially unique. The certificate, in addition to the image of the stone, may also include other information, such as an encrypted code, as discussed below. Thus, both the stone and the accompanying certificate may include identifying information.

Thus, the present invention also encompasses secure certificates, i.e., documents which are tamper and copy resistant, bearing an image of a marked stone, security features, and authentication features. Known secure documents and methods for making secure documents and/or markings are disclosed in U.S. Pat. Nos. 5,393,099; 5,380,047; 5,370,763; 5,367,319; 5,243,641; 5,193,853; 5,018,767; 4,514,085; 4,507,349; 4,247,318; 4,199,615; 4,059,471; 4,178,404; and 4,121,003, expressly incorporated herein by reference. U.S. Pat. No. 4,414,967, expressly incorporated herein by reference, discloses a latent image printing technique, which may be used to form an image of a workpiece. U.S. Pat. Nos. 5,464,690 and 4,913,858, expressly incorporated herein by reference, relate to certificate having holographic security devices.

In another scheme, a stone may be authenticated without the certificate of authenticity, e.g., by a typical jeweler employing simple tools, such as a jeweler's loupe and telephone. Therefore, according to one embodiment of the invention, a jeweler uses a loupe to read an alphanumeric inscription, invisible to the naked eye, on a gemstone. The alphanumeric inscription, or a portion thereof, includes identifying information about the gemstone, e.g., a serial number, which is entered into an authentication system, e.g., by a telephone keypad. The characteristics of the stone, determined at or around the time of the marking process, are then retrieved from a database. In general, these stored characteristics may include grading, size, identification and possible location of flaws, and an image of the stone, including unique or quasi-unique features. Thus, for example, an image of the marking and stone or portions of the stone, e.g., surrounding landmarks of the stone may be stored. Some or all of these characteristics may then be provided to the jeweler, such as by voice synthesis, telefacsimile of the image, or otherwise. Where a certificate of authenticity is available, the certificate may be recreated and a facsimile transmitted to the jeweler, allowing verification of all information contained thereon. The jeweler then compares the retrieved metrics and indicia with those of the stone. If the stone corresponds to the stored information, the stone is likely genuine. If, on the other hand, the stone does not correspond to the stored information, it is possible that the stone is a forgery.

In another embodiment, the authentication system requests a series of measurements from the jeweler, which may be obtained by micrometer or reticle in a loupe, without providing the nominal values to the jeweler, so that no explanation is provided for a failure to authenticate, making forgery more difficult. Of course, the system may also employ more sophisticated equipment for measuring characteristics of the stone and for communications, including a fully automated analysis and communications system.

In another embodiment, the gemstone is self authenticating. Thus, instead of comparison with metric data stored in a database system, the marking inscribed on the stone itself includes an encrypted message containing data relating to characteristics of the stone. A number of different types of messages may be employed. For example, a so-called public key/private key encryption protocol, such as available from RSA, Redwood Calif., may be used to label the workpiece with a "digital signature". See, "A Method for Obtaining Digital Signatures and Public Key Cryptosystems" by R. L. Rivest, A. Shamir and L. Adelmann, Communications of ACM 21(2):120–126 (February 1978), expressly incorporated herein by reference. In this case, an encoding party codes the data using an appropriate algorithm, with a so-called private key. To decode the message, one must be in possession of a second code, called a public key because it may be distributed to the public and is associated with the encoding party. Upon use of this public key, the encrypted message is deciphered, and the identity of the encoding party verified. The data in the deciphered message includes a set of unique or quasi unique characteristics of the gemstone. Therefore, one need only compare the information from the decoded message with the stone to verify the origin of the gemstone and its authenticity. In this scheme, the encoding party need not be informed of the verification procedure. Known variations on this scheme allow private communications between parties or escrowed keys to ensure security of the data except under exceptional authentication procedures.

Typical encryption and document encoding schemes which may be incorporated, in whole or in part, in the system and method according to the invention, to produce secure certificates and/or markings, are disclosed in U.S. Pat. Nos. 5,426,700 (and 07/979,081); 5,422,954; 5,420,924; 5,388,158; 5,384,846; 5,375,170; 5,337,362; 5,263,085; 5,191,613; 5,166,978; 5,163,091; 5,142,577; 5,113,445; 5,073,935; 4,981,370; 4,853,961; 4,893,338; 4,995,081; 4,879,747; 4,868,877; 4,853,961; 4,816,655; 4,812,965; 4,637,051; 4,507,744; and 4,405,829, expressly incorporated herein by reference. See also, W. Diffie and M. E. Hellman, "New directions in cryptography", IEEE Trans. Information Theory, Vol. IT-22, pp. 644–654, November 1976; R. C. Merkle and M. E. Hellman, "Hiding information and signatures in trapdoor knapsacks", IEEE Trans. Information Theory, Vol. IT-24, pp. 525–530, September 1978; Fiat and Shamir, "How to prove yourself: practical solutions to identification and signature problems", Proc. Crypto 86, pp. 186–194 (August 1986); "DSS: specifications of a digital signature algorithm", National Institute of Standards and Technology, Draft, August 1991; and H. Fell and W. Diffie, "Analysis of a public key approach based on polynomial substitution", Proc. Crypto. (1985), pp. 340–349, expressly incorporated herein by reference.

Another encoding scheme uses a DES-type encryption system, which does not allow decoding of the message by the public, but only by authorized persons in possession of the codes. This therefore requires involvement of the encoding party, who decodes the message and assists in stone authentication.

In order to provide enduring authentication, it may be desired that multiple codes, containing different information in different schemes, be encoded on the gemstone, so that if the security of one code is breached or threatened to be breached, another, generally more complex code, is available for use in authentication. For example, a primary code may be provided as an alphanumeric string of 14 digits. In addition, a linear bar code may be inscribed with 128–512 symbols. A further 2-D array of points may be inscribed, e.g., as a pattern superimposed on the alphanumeric string by slight modifications of the placement of ablation centers, double ablations, laser power modulation, and other subtle schemes which have potential to encode up to about 1k–4k symbols, or higher, using multivalued modulation. Each of these increasingly complex codes is, in turn, more difficult to read and decipher.

The ablation pattern of the marking is subject to random perturbations due to both system limitations and surface variations of the stone. Thus, even with a self authenticating code, it is generally desired to store image information relating to the stone in a database after the marking process is completed. This database may then be used for further verification or authentication by image comparison or feature extraction.

Thus, a number of authentication schemes may be simultaneously available. Preferably, different information is encoded by each method, with the more rudimentary information encoded in the less complex encoding schemes. Complex information may include spectrophotometric data, image information, and geometric dimensional topology. Thus, based on the presumption that deciphering of more complex codes will generally be required at later time periods, equipment for verifying the information may be made available only as necessary.

Known techniques for using ID numbers and/or encryption techniques to preventing counterfeiting of secure certificates or markings are disclosed in U.S. Pat. Nos. 5,367,148; 5,283,422; 4,494,381; 4,814,589; 4,630,201 and 4,463,250, expressly incorporated herein by reference.

It is also noted that information may also be stored holographically in crystalline matter. Therefore, in accordance with the present invention, authentication holographic data may be stored within a crystal. The techniques for forming and reading such holographically encoded messages are known, and the use of such encoded messages to authenticate gemstones is a part of the present invention. Thus, the information may be stored as a hologram within the crystalline structure of the stone, or as a relief or phase hologram on a certificate. Therefore, a hologram may be formed directly from the gemstone, preferably optically enlarged. Since the laser markings comprise ablation spots, these will be apparent in the hologram. Further, since the marking process includes a laser, this same laser may be used to expose the hologram, using a modified optical system. For example, a pair of chromate holograms may be individually formed for each gemstone, one placed on the certificate and the other stored with the originator of the marking. The certificate may also include known security features.

Where an original hologram of the workpiece is available, authentication may be automated by optically correlating the hologram and the workpiece. This method will be very sensitive to subtle changes in the workpiece, and thus particularly tamper proof. Preferably, the optical correlation pattern of the hologram and the workpiece is stored after generation or developing the final hologram, in order to compensate for any changes during processing. This optical correlation pattern may be stored photographically or digitally.

Therefore, it is a characteristic of this aspect of the invention that, in order to identify a gemstone, the information stored thereon identifies a database record relating to the stone, and including information relating thereto, or the stored information itself relates to characteristics of the stone.

In one aspect of the invention, the imaging system is ordinarily disposed to view both a portion of the girdle of the stone and a profile thereof. Therefore, it is generally desirable to derive the required information relating to the stone from the imaging system while the gemstone is mounted in the apparatus. Where the inscription itself includes encoded characteristics, these may be applied by the apparatus by imaging the stone through the imaging system, and applying an inscription based on the imaging system output, i.e., by using feedback positioning. An image of the inscribed stone may also be obtained and stored. As stated above, the inscription may be explicitly encoded with readily apparent information, such as an inscribed alphanumeric code, or may include covert information, such as ablation spot placement with respect to stone landmarks, beam modulation, spacing between distant ablation spots, and pseudorandom ablation markings. The markings may also include indicia made at critical portions to allow repeatable measurements, such as edge margins of the girdle.

According to one method of the invention, a gemstone to be marked is imaged, with the image analyzed and extracted information compared to information in a database. Preferably, the database is a central database, remote from the marking apparatus, and the stored information is in digital form. The image is compared to data relating to at least a subset of images of comparable gemstones. An encoded marking is then proposed for a location on the girdle of the stone which, is either absolutely unique, or unique when taken with an easily defined characteristic of the stone. The database system is employed to prevent identical markings on comparable gemstones, and thus fails to approve a proposed marking if it is too similar to any other stone in the database. Thus, according to this aspect of the invention, each stone has a unique coding, and only rarely will a stone be found which is capable of receiving an identical marking to a previously inscribed stone while meeting the same coding criteria. In a simple embodiment, the database assigns a unique serial number to each stone and prevents use of duplicate serial numbers. On the other hand, in a more complex scheme, serial numbers need not be unique if other characteristics of the stone may be used to distinguish candidates.

According to another aspect of the invention, the inherent limitations on the accuracy and repeatability of the marking process are employed to provide a unique encoding of a gemstone. Thus, the surface imperfections of the girdle and the ablation process itself interact to prevent a theoretically ideal marking. Because these effects may be due to vibration, power line fluctuations, laser instability and the like, they will tend to be random over a number of marking operations. These effects will also result from characteristics of the stone. Thus, an attempt to recreate a marking to a high level of detail, even with advanced equipment, will invariably be met with difficulty. Thus, by storing high resolution images of the actual marking, possibly including off axis images or defocused images to gain ablation depth information, authentication of the markings is possible.

In like manner, intentional or "pseudorandom" irregularities (seemingly random, but carrying information in a data pattern) may be imposed on the marking, in order to encode additional information on top of an a marking pattern. Such irregularities in the marking process may include beam modulation, double ablations, fine changes in ablation position, varying degrees of overlap of ablation locations, varying laser focus during pulses. Without knowledge of the encoding pattern, the positional irregularities will appear as random jitter and the intensity irregularities will appear random. Because a pseudorandom pattern is superimposed on a random noise pattern, it may be desirable to differentially encode the pseudorandom noise with respect to an actual encoding position or intensity of previously formed markings, with forward and/or backward error correcting codes. Thus, by using feedback of the actual marking pattern rather than the theoretical pattern, the amplitude of the pseudorandom signal may be reduced closer to the actual noise amplitude while allowing reliable information retrieval. By reducing the pseudorandom signal levels and modulating the pseudorandom signal on the actual noise, it becomes more difficult to duplicate the markings, and more difficult to detect the code without a priori knowledge of the encoding scheme.

While alphanumeric codes and other readily visible codes may be read by common jewelers, subtle encoding methods may require specialized equipment for reading. Therefore, another aspect of the invention provides an automated system for reading codes inscribed on a gemstone. Such a system operates as a video microscope with image analysis capability. The image analysis capability will generally be tuned or adapted for the types of coding employed, reducing the analysis to relevant details. Therefore, where a pseudorandom code appears in the ablation pattern, the individual ablation locations and their interrelations are analyzed. Likewise, where ablation depth or amplitude is relevant, confocal microscopy may be employed.

In like manner, a certificate of authenticity may be provided with authentication and security coding, to prevent forgery or counterfeiting. In addition to the techniques discussed above, a number of other known techniques are available for the tamper and copy protection of documents. In this case, the certificate adds an additional level to the security of the marking process. Therefore, while the workpiece preferably includes a secure marking which does not require a certificate of authenticity for authentication, the addition of the certificate eases the authentication process while making forgery more difficult.

A typical electronic reading device for a gemstone inscription will include a CCD imaging device with a high magnification lens, e.g., about 200 times magnification, and an illumination device. Apparent resolution of the CCD may be increased by multiframe averaging with slight shifts of the gemstone with respect to the CCD optical system. A computer system with a frame grabber or a tele-video system (e.g., a videoconferencing system) may be used to obtain the data and analyze it. In general, known image processing schemes may be used to extract the encoded information.

In addition to being analyzed for information content, i.e., the markings, the workpiece image may also be compared with an image stored in a database. Therefore, based on a presumptive identification of a gemstone, an image record in a database is retrieved. The image of the presumptive gemstone is then compared with the stored image, and any differences then analyzed for significance. These differences may be analyzed manually or automatically. Where a serial number or other code appears, this is used to retrieve a database record corresponding to the stone which was properly inscribed with the serial number or code. Where the code corresponds to characteristics of the stone and markings, more than one record may be retrieved for possible matching with the unauthenticated stone. In this case, the information in the database records should unambiguously authenticate or fail to authenticate the stone.

According to another aspect of the invention, the laser energy microinscribing system includes a semiconductor excited Q-switched solid state laser energy source, a cut gemstone mounting system, having an aperture, an optical system for focusing laser energy from the laser energy source, through said aperture onto a cut gemstone, a displaceable stage for moving said gemstone mounting system with respect to said optical system so that said focused laser energy is presented to desired positions on said gemstone, having a control input, an imaging system for viewing the gemstone from a plurality of vantage points, and a rigid frame supporting said laser, said optical system and said stage in fixed relation, to resist differential movements of said laser, said optical system and said stage and increase immunity to vibrational misalignments. By employing a laser system with low cooling and power requirements, the device may be made self contained and compact. By minimizing the size of the apparatus, and enclosing the device in a rigid frame or chassis, vibration immunity is improved. Thus, as compared to systems employing flashlamp excited lasers, substantial vibration isolation apparatus is eliminated.

According to another aspect of the invention, prior to any marking operation, the proposed marking and/or the presumed resulting image are compared to database records to determine if the proposed marking and/or resulting marked gemstone are too close to any previously marked gemstone to be easily distinguished. If so, the marking or proposed marking may be altered. In addition, as an automatic feature of the machine, this comparison may prevent use of an authorized machine to counterfeit a previously marked gemstone, and will insure the integrity of the database.

According to another aspect of the invention, a pattern marking is inscribed on a portion of the gemstone, such as a girdle. Because it is difficult to recreate a particular girdle pattern exactly, the pattern will allow, for example with a loupe, quantification of girdle characteristics, including width, contour and size. Thus, the pattern assists in providing a metric for gemstone authentication.

The database may be stored locally to the marking apparatus, but preferably a central database is maintained, receiving identification and/or image information from many remote marking locations, and allowing central control and retrieval of records. This also facilitates a separation of function to maintain the integrity of the system and long term authentication procedures.

OBJECTS OF THE INVENTION

It is therefore an object of the invention to provide a laser energy microinscribing system, comprising a pulse laser energy source; a workpiece mounting system, having an optical aperture; an optical system for focusing laser energy from the laser energy source, through said optical aperture onto a workpiece; means for directing said focused laser energy onto a desired portion of the workpiece, having a control input; an imaging system for viewing the workpiece from a plurality of vantage points; an input for receiving marking instructions; a processor for controlling said directing means based on said marking instructions and information received from said imaging system, to generate a marking in accordance with said instructions; and a storage system for electronically storing information relating to images of markings on a plurality of workpieces.

It is also an object of the invention to provide a method of microinscribing a workpiece with laser energy from a pulse laser energy source, focused by an optical system on the workpiece, comprising the steps of mounting a workpiece in a mounting system; directing the focused laser energy onto a desired portion of the workpiece; electronically imaging the workpiece from a plurality of vantage points; receiving marking instructions from an input; controlling the directing of the focused laser energy based on the marking instructions and the electronic imaging, to generate a marking in accordance with said instructions; and storing electronic information relating to images of markings on a plurality of workpieces.

It is a still further object of the invention to provide a laser energy microinscribing system, comprising a semiconductor excited Q-switched solid state laser energy source; a cut gemstone mounting system, having an aperture; an optical system for focusing laser energy from the laser energy source, through said aperture onto a cut gemstone; a displaceable stage for moving said gemstone mounting system with respect to said optical system so that said focused laser energy is presented to desired positions on said gemstone, having a control input; an imaging system for viewing the gemstone from a plurality of vantage points; and a rigid frame supporting said laser, said optical system and said stage in fixed relation, to resist differential movements of said laser, said optical system and said stage and increase immunity to vibrational misalignments.

These and other objects will become apparent. For a fuller understanding of the present invention, reference should now be made to the following detailed description of the preferred embodiments of the invention as illustrated in the accompanying drawings.

BRIEF DESCRIPTION OF THE DRAWINGS

The invention will now be described with respect to the drawings of the Figures, in which:

FIGS. 7A, 7B, 7C, 7D, and 7E are various views of a workpiece mounting system according to the present invention;

DETAILED DESCRIPTION OF THE PREFERRED EMBODIMENTS

Figure 1:
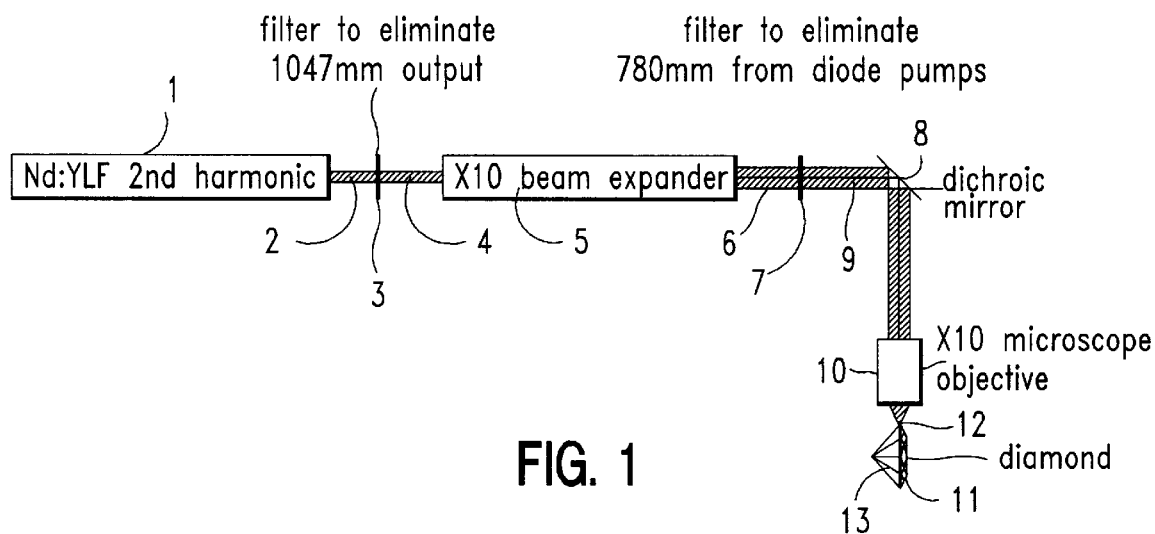
FIG. 1 is a diagram of the laser optical path of the system according to the present invention.

The detailed preferred embodiments of the invention will now be described with respect to the drawings. Like features of the drawings are indicated with the same reference numerals.

The system according to the present invention may be used to micro-inscribe alpha/numeric characters on the girdle of diamonds 13. It is based on a pulse laser 1, and preferably a Q-switched laser diode pumped solid state laser, to provide minimum volume and installation requirements, and optimum compatibility with any office environment.

A preferred laser based inscribing system according to the present invention thus contains the following primary elements:

In a vibration isolated frame 140 with shock absorbers 141, at the positions of support:

(1) Laser diode pumped laser 1 and programmable power supply 14, with a Beam Expander 5.

(2) Optical assembly containing guiding 8 and focusing optics 10, miniature CCD cameras 28, 32 and illumination system.

(3) XYZ motion stages 50 (with Z elevator stage) including encoders 145, limits and DC brushless motors.

(4) Diamond holder 144 and accessories (5) Enclosure 142 with safety interlock 143 to prevent operation with open cabinet and to prevent stray or scattered laser energy from posing a safety hazard.

(6) Computer system 52 for control:
   (a) PC (Pentium 100 Mhz), PCI bus, 1024 by 768 VGA monitor
   (b) Frame grabber 56 (Matrox, videographic card).
   (c) 3-axis motion controller card 60.
   (d) Cables, Power Supplies.
   (e) System operation software (Windows).
   (f) Application Software Apparatus As shown in FIG. 1, a Nd:YLF $2^{nd}$ harmonic laser 1 (QD321) is provided, which emits a beam 2 having about 525 nm wavelength. A 1047 nm filter 3 is provided to attenuate any residual fundamental laser output energy, to produce a filtered laser beam 4. The filtered beam is then expanded in a ten-times beam expander 5 to reduce energy density. In the path of the expanded beam 6, a 780 nm filter 7 is provided to eliminate energy from the diode pumps. A dichroic mirror 8 reflects the expanded, filtered beam 9 toward a ten-times microscope objective 10. The microscope objective 10 focuses the beam onto the workpiece 11, which is for example a girdle 12 of a cut diamond 13.

Figure 2:
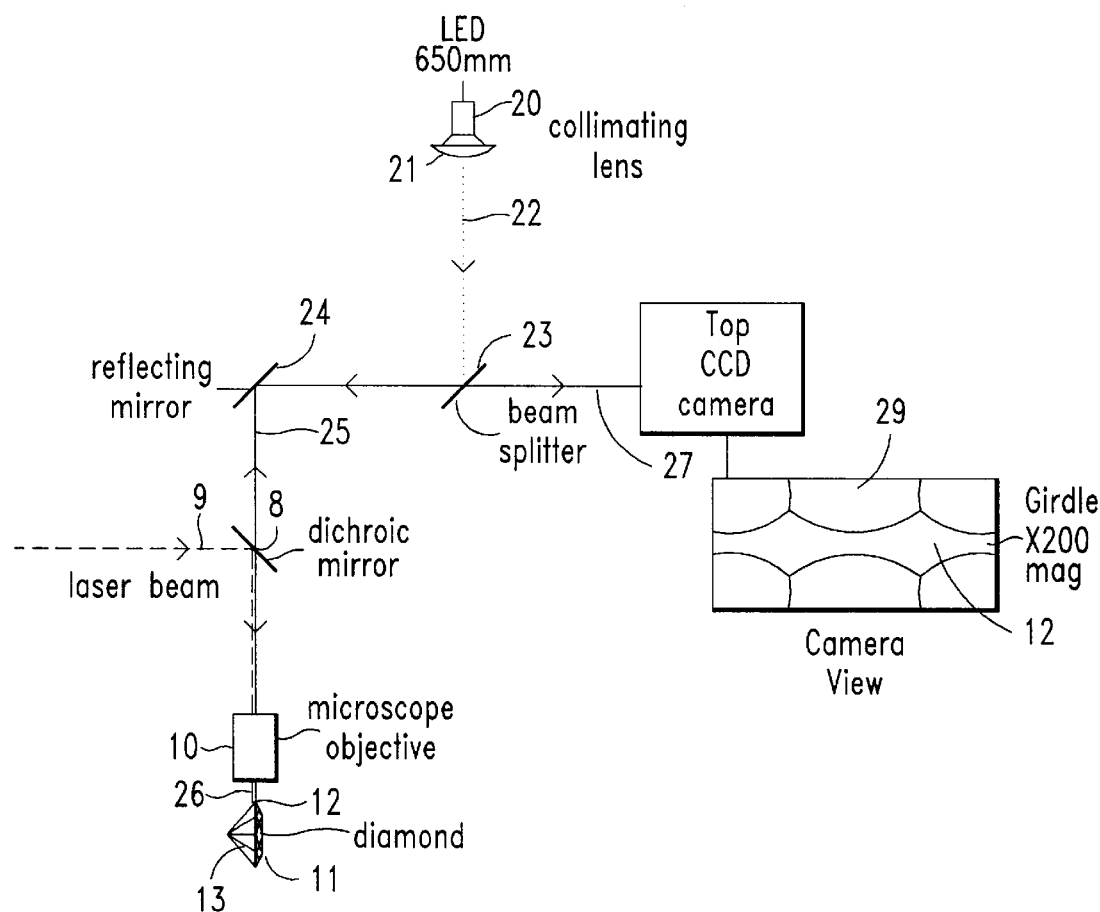
FIG. 2 is a diagram of the top illumination and imaging systems according to the present invention.

FIG. 2 shows the top illumination and imaging systems. An LED 20 or array of LEDs having emission at about 650 nm projects through a collimating lens 21 to produce a collimated illumination beam 22. The collimated illumination beam 22 projects on a beam splitter 23, which reflects the collimated illumination beam 22 toward a reflecting mirror 24. The reflected collimated illumination beam 25 passes through the dichroic mirror 8, parallel to the filtered beam 9, and through the microscope objective 10 onto the workpiece 11. The workpiece 11 reflects a portion of the illumination beam back through the microscope objective 10 and through the dichroic mirror 8, onto the reflecting mirror 24, tracing an opposite path from the collimated illumination beam 25. A portion of the reflected illumination beam 27, however, passes through the beam splitter 23, toward a top CCD camera 28. Thus, the top CCD camera 28 views the workpiece 11 with the 650 nm illumination. When displayed on a 14 inch video monitor 159, the resulting magnification of the image 29 is about 200 times.

Figure 3:
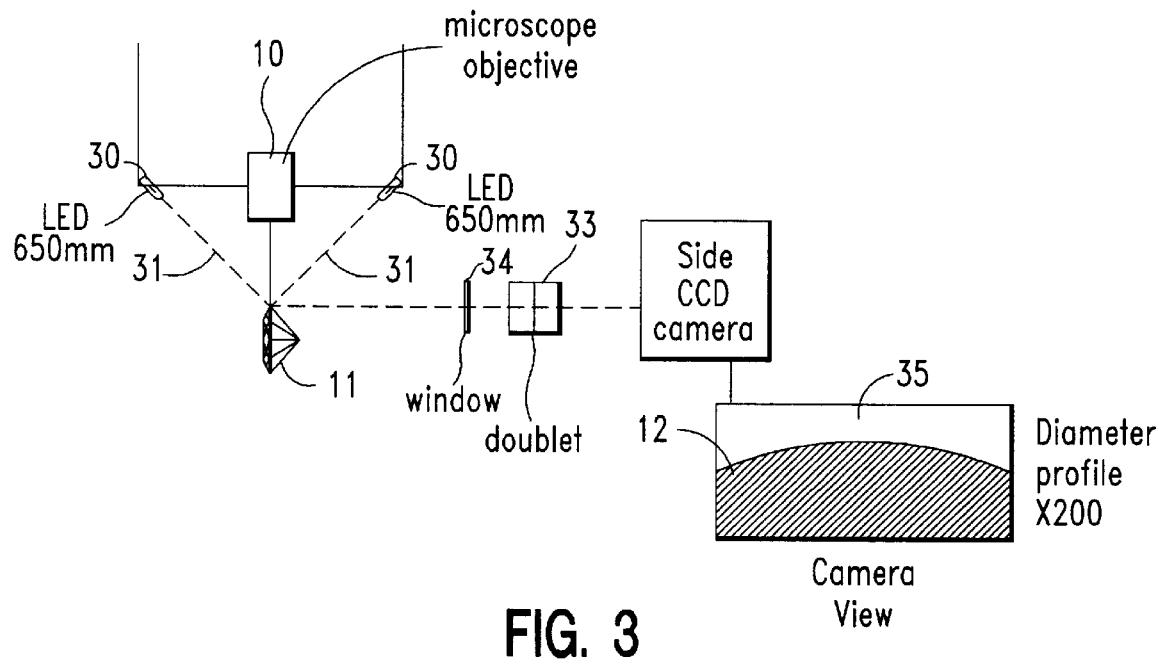
FIG. 3 is a diagram of a side illumination and imaging systems according to the present invention.

The side illumination and imaging systems, shown in FIG. 3 is somewhat simpler than the top illumination and imaging systems shown in FIG. 2. A set of spaced 650 nm LEDs 30 produce illumination 31 at angles generally converging from the top toward the workpiece 11. A side CCD camera 32, views the workpiece 11 through a doublet lens 33 and window 34, at right angles to the top CCD camera 28. The resulting image 35 of the side CCD camera 32 on a 14 inch video monitor is also about 200 times magnification. Where the workpiece 11 is a cut diamond 13 having a girdle 12, the side image 35 includes the profile of the girdle 12'.

Figure 4:
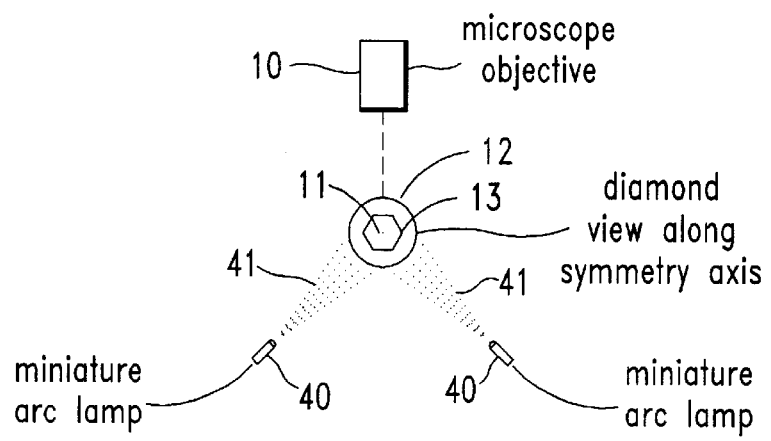
FIG. 4 is a diagram of a bottom illumination system according to the present invention.

The bottom illumination system, shown in FIG. 4 includes a set of spaced miniature arc lamps 40 below the workpiece 11, producing illumination along paths 41 which are upwardly converging.

Figure 5:
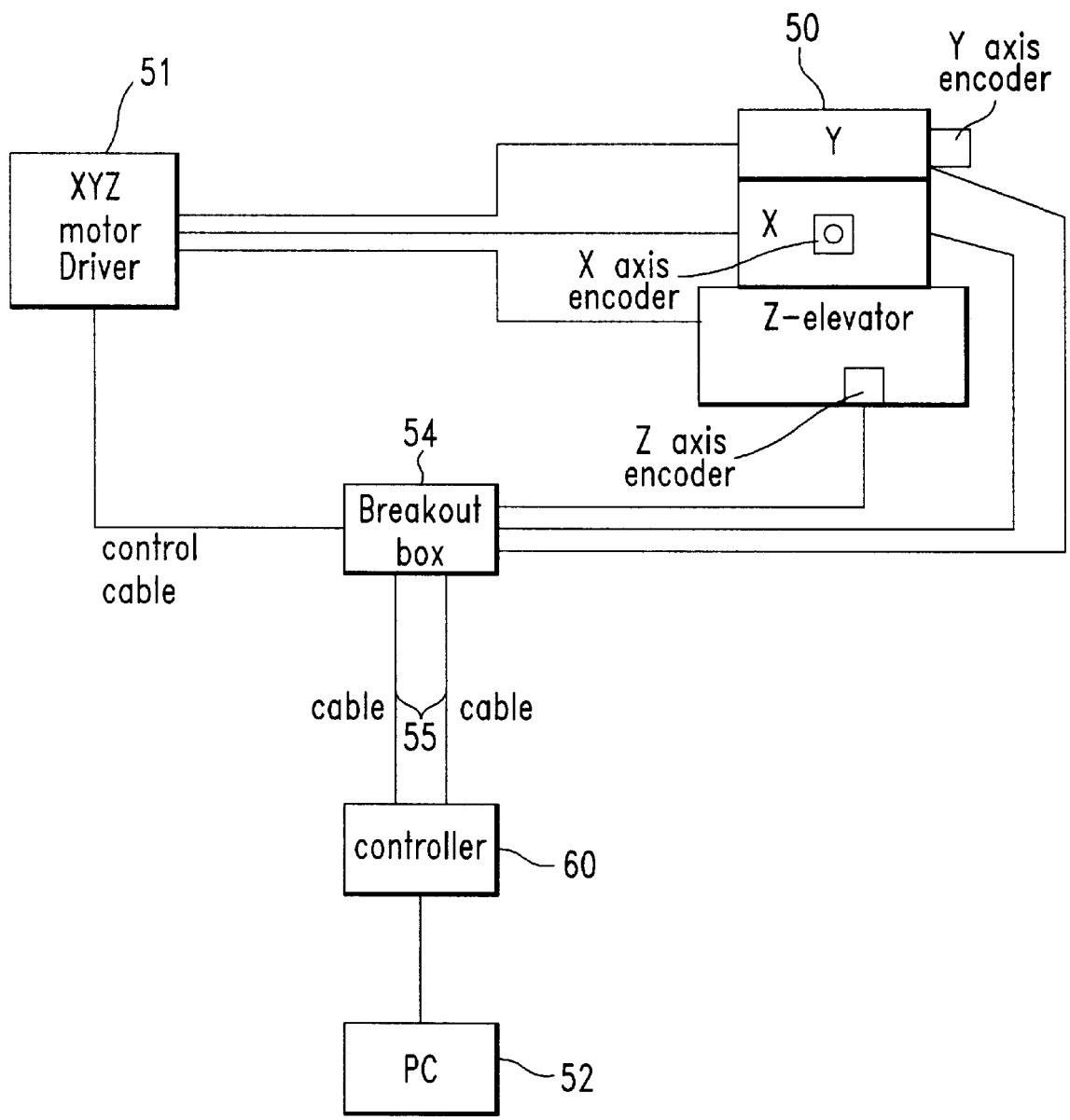
FIG. 5 is a block diagram of the stage positioning system and control according to the present invention.

The stage positioning and control system is shown in FIG. 5. The workpiece is mounted on a three axis stage 50, with encoder feedback in a workpiece mount assembly 144. The drivers 51 for the three axis stage are provided within the laser system enclosure 142, separate from the computer control 52. The computer control 52 communicates through a positioning control system 53 (Galil), which is an ISA bus card. A breakout box 54 is provided within the laser system enclosure 142, which is connected by a set of cables 55 to the positioning control system 53.

Figure 6:
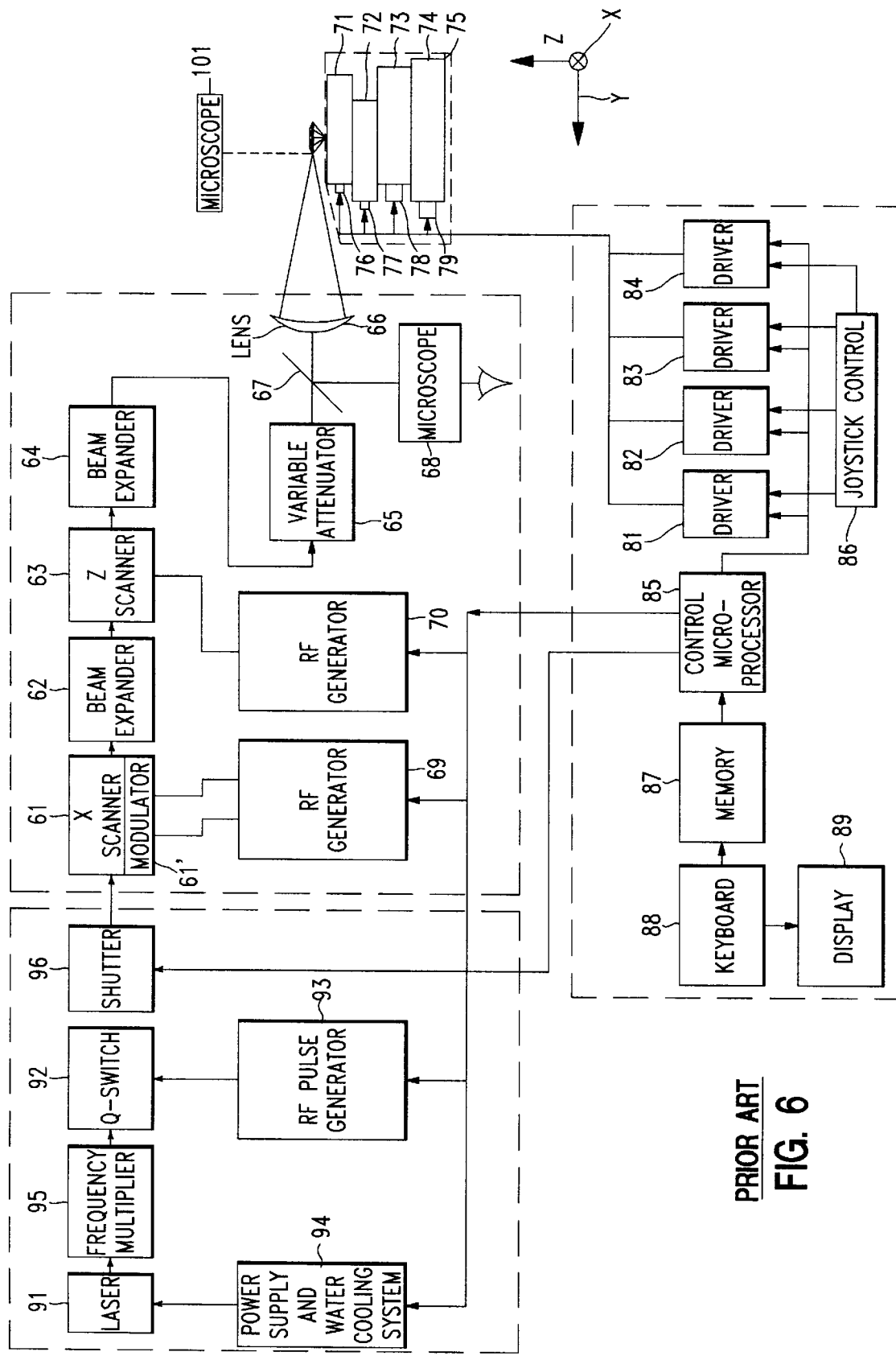
FIG. 6 is a diagram of a prior art beam steering system.
Figure 7A:
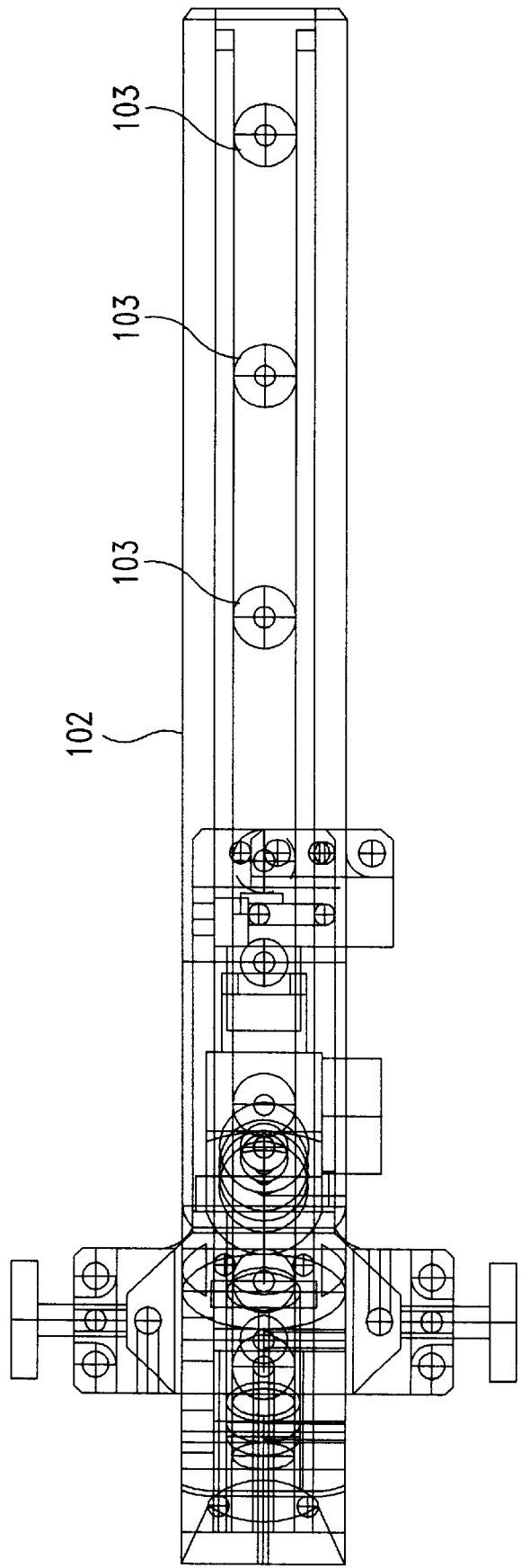
Figures 7B, 7C:
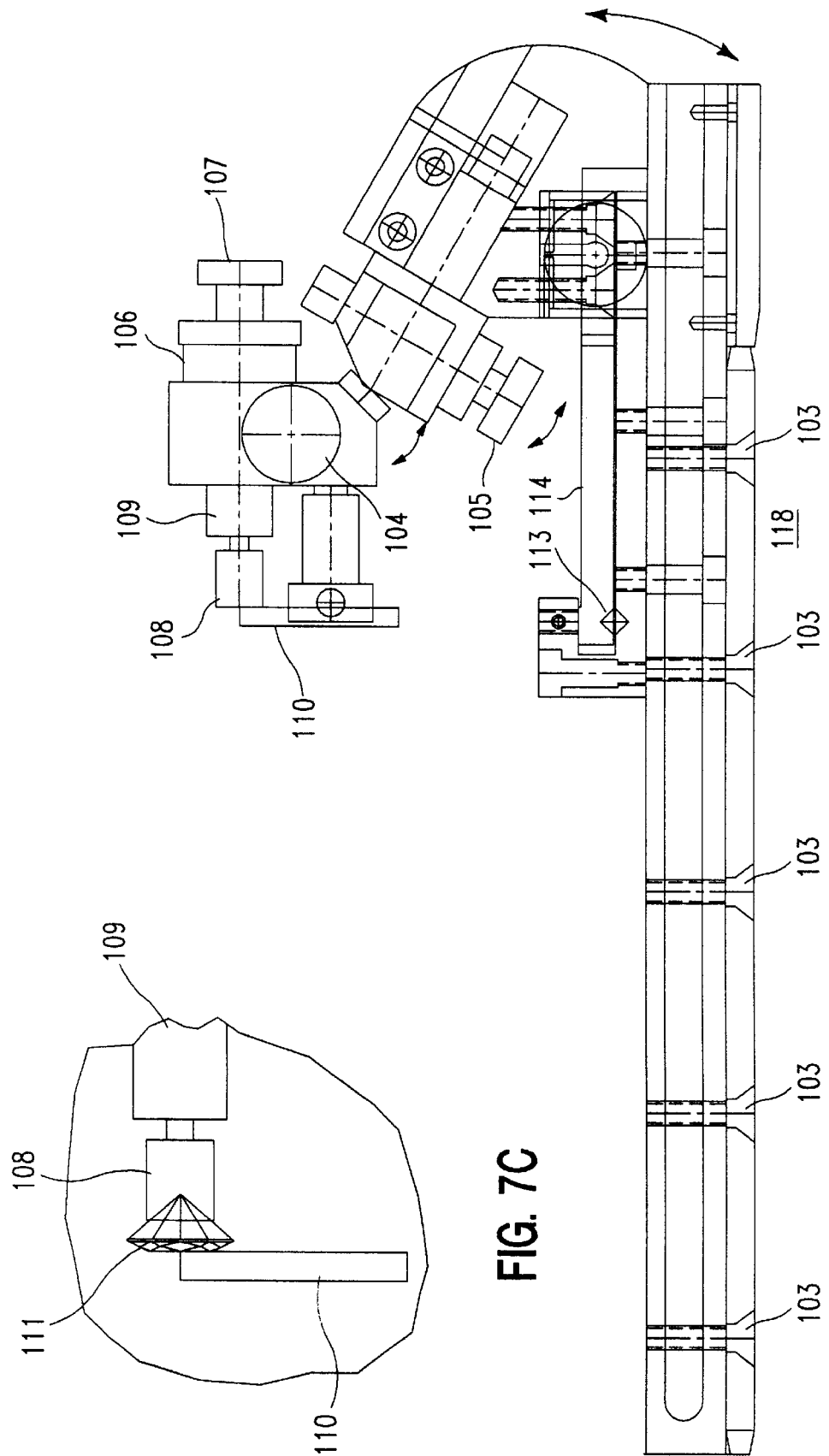
Figure 7E:
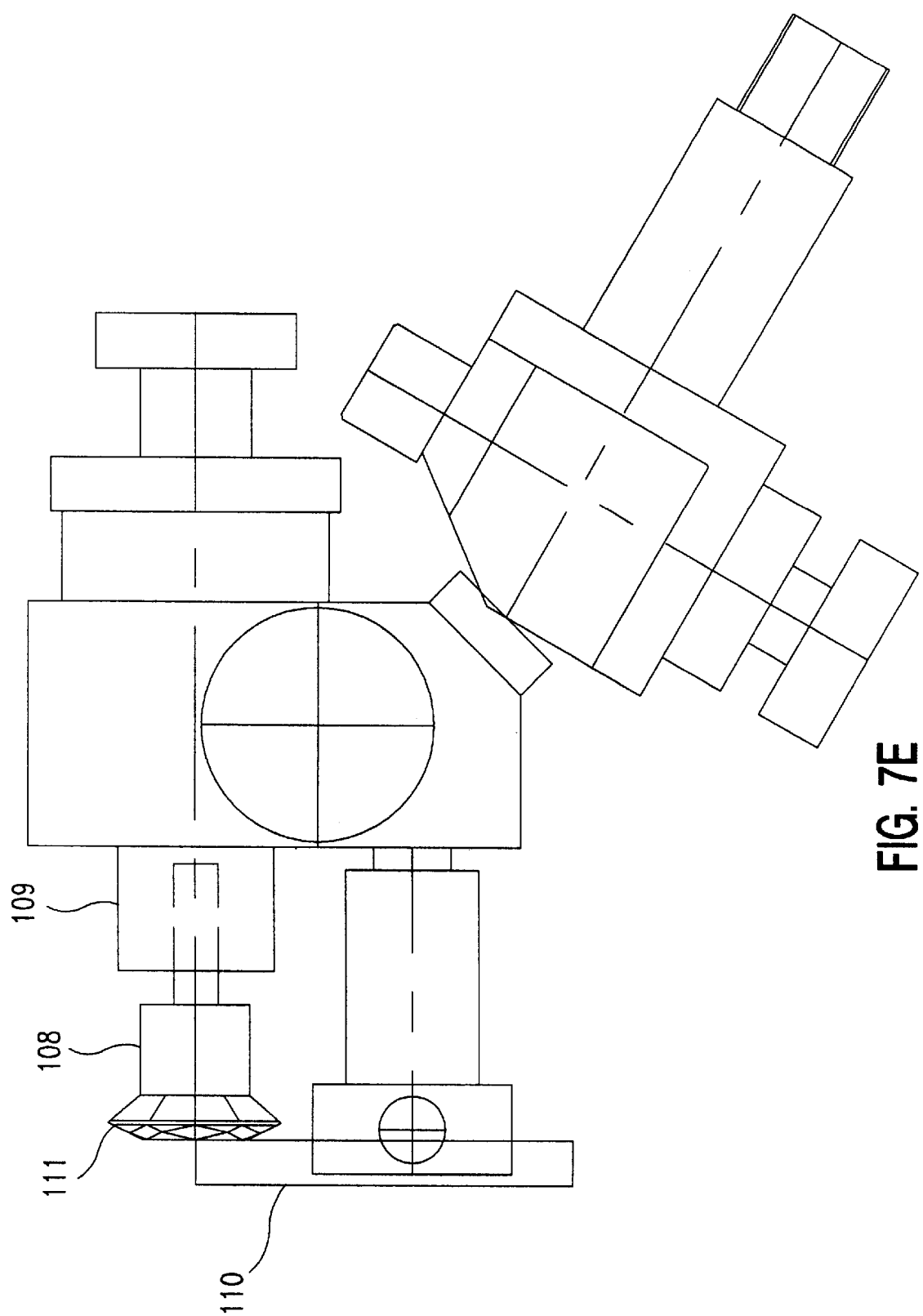

As shown in FIG. 6 (prior art), a known system described in U.S. Pat. No. 4,392,476 includes an X scanner 61 and a Z scanner 63, which steer the laser beam onto the diamond 13. This known system has limited repeatability. Further, the system is relatively large, and subject to vibrational influences.

FIGS. 7A–7E show the diamond holder in top, side, side detail, mounted stone holder, and unmounted stone holder, respectively. A slide 116 allows precise positioning with respect to a slot, within the cabinet. The slide 116 is positioned by a set of hardened steel balls and spring loaded balls which positions the holder 116 as it is inserted into the slot. A set of manual adjustments allow control over coarse 106 and fine 104 rotation, with a lock/release chuck 107 provided. The workpiece 11 is set in a pot 108 mounted in a chuck 109, with two round rods positioning the workpiece, held in place by a finger 110.

As shown in FIG. 7D, a mounted workpiece holder allows a mounted workpiece 111 to be held precisely. A spring loaded trigger 112 is provided to allow mounting and unmounting of the mounted workpiece.

Mode of Operation

The system includes a static laser beam, e.g., a laser beam generation apparatus which does not move. The XYZ positioning system 50 moves the workpiece 11 and generates the inscription with repeatability and resolution of about 1.0 microns. The beam size at the focal point is greater than about 1 micron, so that the positioning system 50 accuracy is not the limiting factor in the placement of the marking.

With the axis of symmetry of the workpiece 11, which is for example a diamond 13, horizontally disposed, the diamond girdle 12 is viewed horizontally (profile mode) and vertically (inscription mode) by two CCD cameras 28, 32. The vertical axis also corresponds to the axis of laser 1. A third camera may also be provided, for example having an optical path facing generally upward toward the laser. Of course, an imaging device facing the laser beam is provided in a manner to prevent damage during operation. Due to the focus of the laser 1, as well as filtering optics 8, 23, 34 there is low risk of damage to the CCDs 28, 32 due to laser energy. The user can choose to view one or more cameras. Where multiple images are present, they may be tiled at reduced size on the computer monitor screen 159. Using a mouse 161 as a pointing device, the girdle 12 is centered and focused by viewing the screen 159, using particularly a profile view. The diamond 13 can be manually rotated in its mounting 144 to bring the correct part of the girdle 12 to the center of a display window on the screen 159. The images are provided with a magnification of about 200 times, although other magnifications or variable magnifications are possible. Magnification is defined herein as the ratio of the inscription size as measured on screen 159 and that of the actual inscription size. In general, a 14 or 15 inch diagonal video monitor is employed, with a resolution of 1024 by 768 pixels.

The user-entered portion of the content of the inscription is typed on a keyboard 148 or entered by a bar-code reader 149 into the computer. Of course, the data entry may also be by voice through a microphone 150 for speech recognition, magnetic strip through reader 151, or through point-and-click operations using a computer mouse 161. The entered inscription and logo are shown on the video screen 159 superimposed on an area corresponding to the girdle 12 of the diamond 13. Using the mouse 161 and keyboard 160, the user can change all inscription characteristics in order to fit it correctly in the girdle 12. While the preferred user interface is a graphic user interface with pointing device (mouse 161), keyboard 160 and display screen 159, where the user's hands may be occupied, a voice-command recognition system may be used, e.g., through microphone 150, with verification of all input information and commencement of operational sequence by a specific sequence of actions by the user in fail-safe manner, so that, e.g., stray noises do not cause catastrophic interference.

In the horizontal camera 32 screen the user can measure the girdle 12 profile, using a mouse input device 161 to mark the critical dimensions. This data is then used to keep the focal point of the laser output on the surface of the girdle 12 at all times. The profile data and girdle 12 outline may be automatically extracted from the images, or a manual entry step employed to outline the profile and/or girdle boundaries. In general, the inscription positioning on the girdle will be manually assisted, although full automation, especially for low value small stones, known as mellee, may be employed. When these procedures are complete a so-called G-code file is generated containing all inscription data. This file is transferred to the positioning stage controller 51 for performance of the actual inscription.

Figure 11:
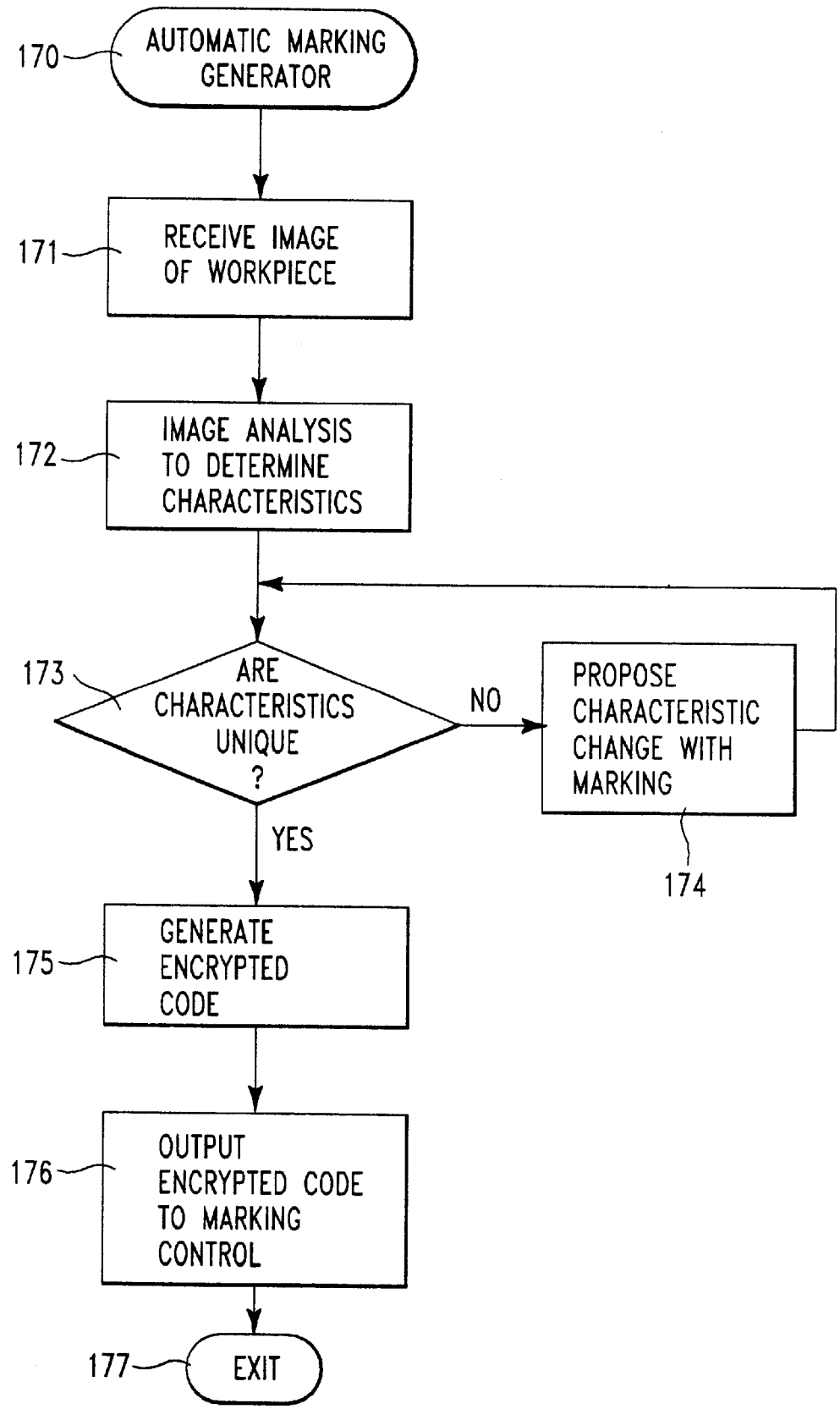
FIG. 11 is a flow chart depicting an automatic marking generating routine according to the present invention.

The inscription code file may optionally be automatically generated and authorized based on an algorithm to prevent unauthorized or fraudulent inscriptions, as depicted in FIG. 11. The authorization process according to one embodiment of the invention includes the steps of obtaining or retrieving an image of the workpiece 171, analyzing the image to determine characteristics of the workpiece 172, transmission of the characteristics in conjunction with data relating to the stone to an authenticator, through, for example, a telecommunications link 152, which may be at a different location, determining whether the characteristics and proposed marking are unique 173, which may be performed remotely, or locally, and if the characteristics and marking are not unique, proposing a change in the marking 174 and then reverifying the modified proposed marking with the authenticator. After a marking is approved, the marking is encrypted 175, and the encrypted code transmitted to the marking control 176. Thus, only if the authenticator approves a marking does the system commence marking.

The characteristics of the workpiece may be determined by eye 146, and may also be determined by a sensor 147 of appropriate type. For example, dimensions, weight, optical transmission characteristics, facet angles and the like may be measured. During the initial marking process, the characteristics are determined, and are preferably stored in conjunction with the marking information in a database 156. For example, this database may store images, compressed images or aspects of images derived from the CCD imagers 28, 32. Preferably, after the marking has occurred, the top CCD imager 28 is used to capture an image of the marking, which is then stored. According to one embodiment of the invention, information stored in the database or marked on the stone may be encrypted using a secure encryption method by means of an encryption processor 157, reducing the risk of fraud. Further, the marking may be, in part, self authenticating by including identification of characteristics of the marked workpiece. Of course, the encryption processor may be the same as the control system 155, and need not be a separate physical device.

The controller executes all I/O operations such as laser on/off, laser power out of range, limit switches, mouse, etc., as well as performing the motion itself. Thus, the control system may easily be upgraded as desired separately from the marking system hardware.

The operator can observe the diamond before, during and after the inscription marking process. In case the inscription is not complete, the operator can choose to repeat all or selected parts of this inscription in a second or subsequent marking operation.

Figure 8:
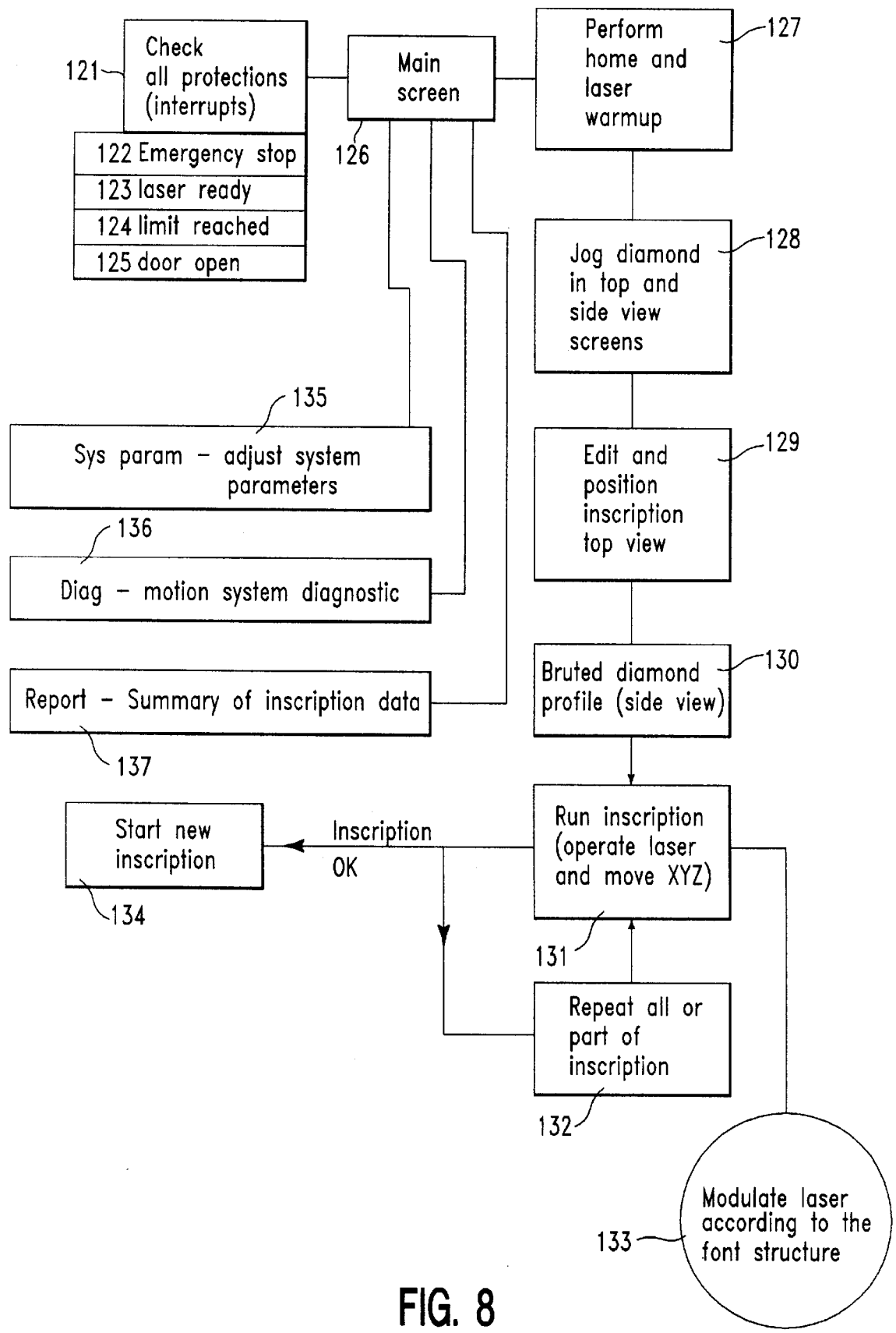
FIG. 8 is a flow chart depicting operation of a system according to a first embodiment of the present invention.
Figure 9:
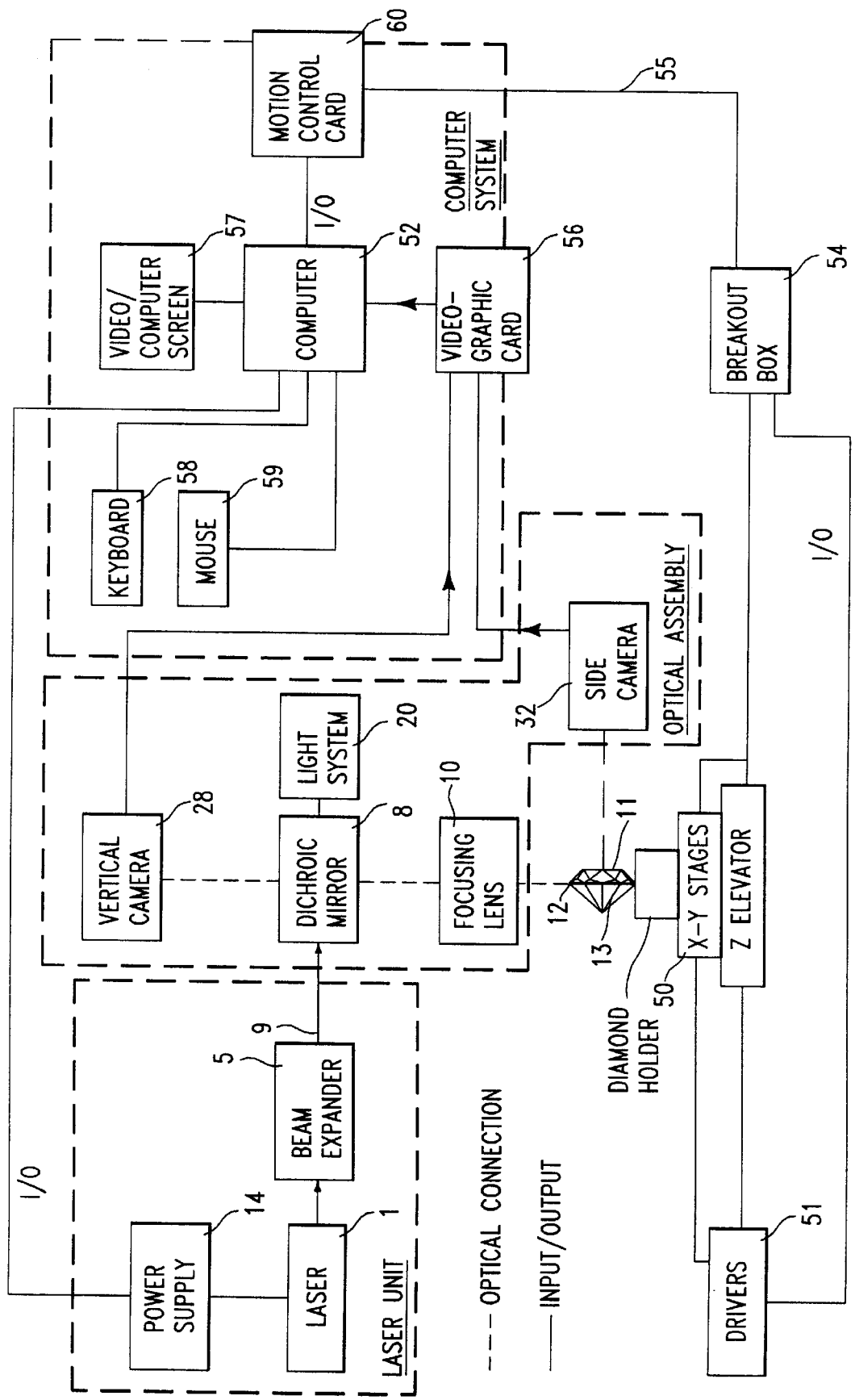
FIG. 9 is a block diagram of an apparatus according to the first embodiment of the present invention.
Figure 10:
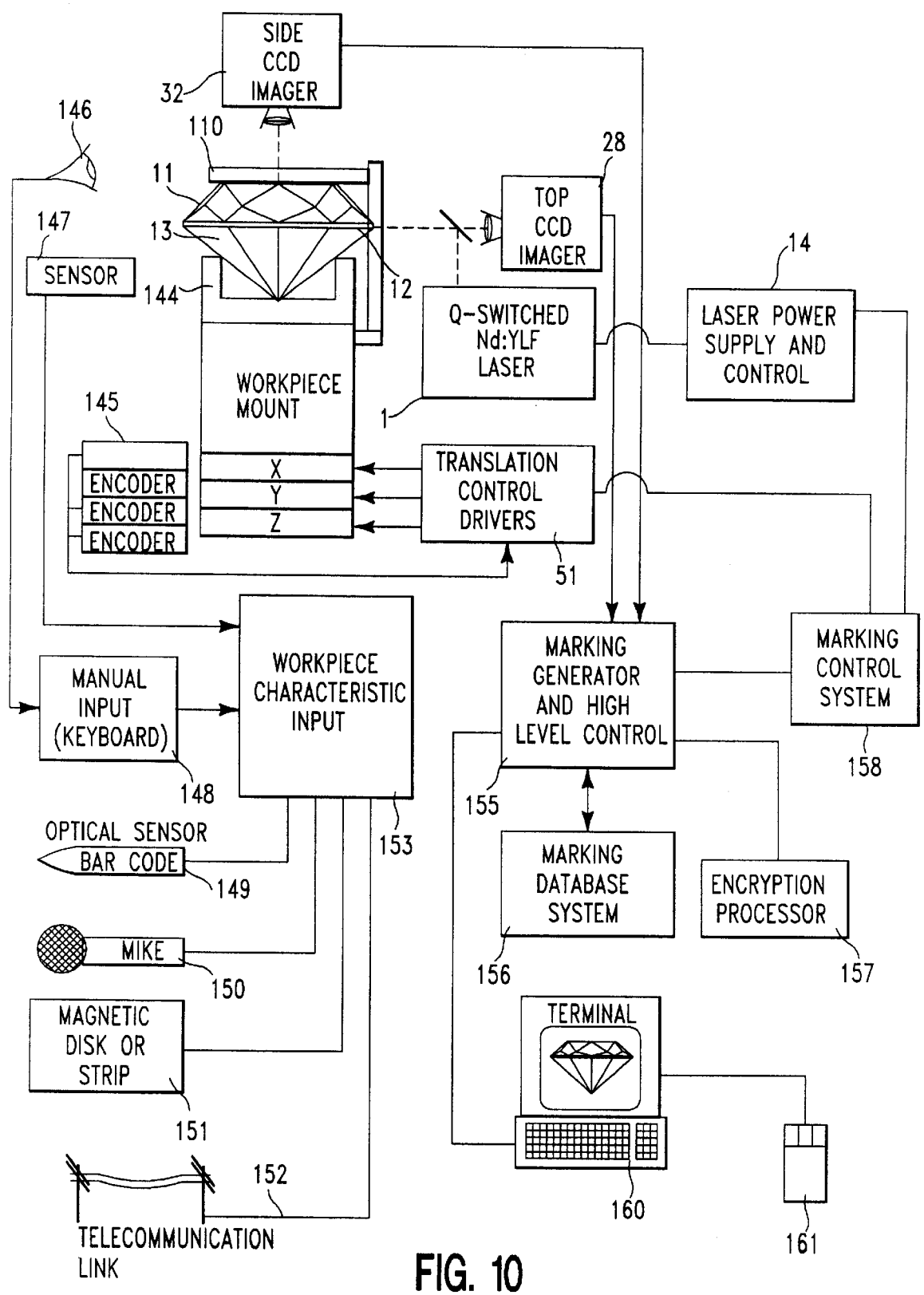
FIG. 10 is a block diagram of an apparatus according to a second embodiment of the present invention.

FIG. 8 shows a flow diagram of the operation of the control system for the laser inscription process. A software module in the control system generates interrupts which sense laser system conditions, and may also initiate action automatically based on those conditions 121. The inputs to the laser system sensing module 121 include emergency stop 122, laser ready 123, mechanical limit reached 124, and door open 125. Of course, other conditions may be sensed and controlled by this sensing module 121.

A main interface screen 126 is provided allowing the operator to access and control the main functionality of the laser inscription system. This interface screen 126 initially controls laser warm up and positioning at a home position 127. After a gemstone is inserted into the laser inscription system, it is jogged into alignment 128 with reference to the top and side views, displayed on the video monitor. Next, the inscription is entered or edited by an input device such as a keyboard 148 or bar code reader 149, and the inscription positioned with respect to the workpiece in the top view 129. If the workpiece has a rough surface, such as a brutted girdle of a diamond, the inscription positioning is verified in the side view 130. The host computer 52 sends commands to the laser inscription controller 60 defining the inscription pattern, by defining XYZ positioning of the workpiece 131 and a pattern of laser modulation 132, in order to define the inscription pattern, e.g., the font or logo structure. After all or a segment of the inscription is made, the inscription is verified to ensure complete inscription, and all or a portion of the inscription may be repeated as necessary 133. The inscription is then complete, and a new inscription process may be commenced 134.

In addition, a maintenance mode of operation is available, which allows adjustment of system parameters 135, motion system diagnostics 136, and a summary report of inscription data 137.

INSCRIPTION SPECIFICATION

The length of inscription depends on size of characters and spacing. Below is a table representing appropriate dimensions:

|  | HEIGHT (microns) | WIDTH (microns) | SPACING (microns) |
|---|---|---|---|
| Large characters | 80 | 60 | 30 |
| Medium characters | 60 | 45 | 25 |
| Small characters | 40 | 30 | 20 |
| Ex. Small chars. | 20 | 15 | 10 |

The total length of inscription=number of characters X (width+spacing)+logo length.

The system accommodates maximum single inscription lengths of approximately 2 mm. At an average of 80 microns per character (including spacing) this gives 25 characters which covers requirements for logo+14 characters. Longer inscriptions can be implemented by consecutive inscriptions without dismounting diamond. In this case there is no limit on number of characters, except by the available surface area. Each logo+14 characters is accounted for as a single inscription process. Inscribing more characters would normally present no problem. It is noted that the characters may be alphanumeric, line-drawing, multi-lingual fonts, custom bitmaps, or other pictorial representations, and may be fully programmable.

The software of the control system also allows any number of inscribed symbols. It is also easy to rotate the stone and position a section of the inscription so that it is or seems to be continuous with the first one. Any symbol size may be produced, within the limits of the line width and surface to be inscribed. For example, with a red beam, the lower limit of symbol size is around 30 microns. With a green beam the lower limit of symbol size is about 15–20 microns.

The depth of inscription is less than about 10 microns.

The line width (green beam) is less than about 9 microns on a polished girdle and less than about 12 microns on a brutted girdle. The system employs a green laser to provide a finer inscription line width than is possible with a standard-type red laser. Start up time for the system is about 15 minutes, mostly accounted for by laser stabilization time, after which the instrument is fully operational, an advantage over other laser types. In a preferred marking method, the irradiated areas overlap, to provide an appearance of continuity of marking.

The laser output is provided as a Q-switched laser, which may be provided in a range of about 1200 to 200 nm, with a frequency doubler or harmonic generator as necessary to provide an output wavelength of less than about 600 nm. A preferred laser 1 is a Q-switched solid state neodynium laser, e.g., a laser diode pumped Nd:YLF laser, operating at 1.06 $\mu$m, with a frequency doubler to provide an output of 530 nm.

Operating according to the system heretofore described, net inscription times (laser time) are estimated to be less than 20 seconds for polished girdles and about less than 35 seconds for brutted girdles.

On polished girdles, inscriptions are generally satisfactory after a first pass. Brutted girdles, on the other hand, may require multiple passes, depending on surface quality, to achieve a desired marking. For time efficiency, multiple runs are executed only on those characters requiring additional runs. These characters can be marked with the mouse. Of course, the reruns may be automatically performed based on a predetermined criteria or based on optical feedback from the video cameras.

Mounting and dismounting the stone is performed using a modular holder 144 with a quick connect socket, and therefore may be accomplished in about 20–30 seconds. The rest of the operations, e.g., locating optimal place for inscription, painting, etc., depend on the manual skill of the operator, and may take about 30–40 seconds. Consequently, 40 stones per hour throughput is possible using the apparatus according to the present invention.

DC brushless motors are employed in the translatable stage system 50. These are driven by a standard-type motor driver system. The X, Y stage employs linear encoders for feedback of stage position, while the Z stage employs a rotary encoder for a helical positioning mechanism.

FONT AND SYMBOL CAPABILITIES

An assortment of characters may be provided with each system, such as an ASCII font set containing 26 letters and 10 numerals, business characters as follows: (TM), (SM), ® and a logo. These font sets are, e.g., available from Borland. Additional fonts, e.g., Japanese and/or Hebrew, and logos may, of course, be employed, e.g., added to the system using removable magnetic media, smart cards, or by digital telecommunication. The font may also include custom or editable characters, allowing full freedom to define a raster bitmap represented by a character identification code. Thus, any figure which can be rendered in lines or a bitmap may be included as a marking.

Inscription data can be entered in three ways:

Manually-alphanumeric symbols entered from the keyboard 148 and logo selected from the logo library.

Semi-automatic—part of the alphanumeric symbols from bar-code 149 or from a keyboard 148 and part of the symbols selected automatically by a serialization counter.

Fully automatic—a complete inscription is generated by the device, after inputting an identification from bar code or similar system.

Using a graphic video overlay, the inscription position and dimensions can be easily adjusted.

The system controller also provides over/under power protection. In case laser power exceeds set limits the system will stop working and issue a warning, thus ensuring that no damage is caused to the diamond or a workpiece.

Vibration dampers 141 are provided at the base of the laser system frame 140. Thus, due to the compact size of the system and relatively small components, the frame 140 may have sufficient rigidity to provide isolation from vibrational effects. Operation is therefore possible in any normal office environment at normal room temperature, without extraordinary measures, such as strict environmental control, or active vibration damping.

The computer 52 is a "PC" type, and is generally provided as a separate enclosure from the laser inscribing system enclosure 142. Generally, two cables 55 connect the computer controller 55 to the laser system enclosure 142, a motion controller and laser control cable and a frame grabber cable. The user may therefore position the screen 159 and keyboard 160 with mouse 161 at the most convenient position.

INSCRIPTION OBSERVATION

The system includes two high resolution miniature CCD cameras with illumination and filter systems for efficient viewing of entire inscription process on a video screen as follows:

The complete inscription with logo is projected on an image from a vertically oriented camera 28 of the girdle 12 providing the user with the ability to interactively change length of inscription, height of characters remove and align the whole inscription. The girdle 12 area may be outlined by the user with a mouse 161 or automatically determined by image analysis in the computer system 52.

The operator can thus observe the inscription before marking; observe the marking process itself, and then observe the result and decide if the inscription is complete or not. A protective enclosure 142 prevents scattered radiation from reaching operator eyes. Filters or the like may also be provided to prevent damage to the video cameras from reflected laser energy.

The operator is provided with complete control of positioning, and inscription allowing approval of the inscription before laser operation. Cursors on the screen help in centering the inscription. The system also has a side camera 32 for girdle 12 profile mapping and table viewing.

The operator marks as many points that are needed on the profile allowing the system to then automatically adjust (Z-axis focal location) to conform to the girdle profile during marking. A manual override is also provided where the automated inscription depth control is not desired.

The side camera 32 allows precise determination of the position of the girdle 12 of the gemstone 11, so that the laser 1 may be focused onto the gemstone 11 surface with high precision. In order to effectively ablate a small surface portion of the gemstone 11, without damaging deeper portions, or producing significant undesired thermal stress effects around the inscription, the laser 1 is provided with a very narrow depth of field, e.g., about 30 $\mu$m. In addition, the small depth of field is required in order to obtain maximum power density from a relatively low power laser 1. Thus, by attempting to focus using a top view only, without a profile view, to achieve focus by maximizing contrast and edge sharpness, user discretion is required and accuracy is limited. In contrast, by providing a side view, the profile of the stone is aligned with a predetermined focal plane, assuring accuracy of about ±7 $\mu$m. In practice, at 200 times magnification, the ±7 $\mu$m corresponds to ±2 pixels of the video imaging camera. Thus, after determining the exact focal plane of the laser 1 empirically, this plane may be provided as a reference in the control system, and the workpiece moved manually or automatically with relative ease to the desired location(s). The reference may appear, for example, as a line on a computer monitor displaying a Z-axis video image of the workpiece. The operator jogs the Z-axis control until the profile of the workpiece 11 in the image is tangent to the reference line.

Vibration and/or impact during, e.g., shipping, may alter the focal plane of the laser with respect to the workpiece mount 144. In this case, a simple "trial and error" or empirical study is conducted to redetermine the exact focal plane, which is then used to provide the correct reference in the control. This calibration study may be conducted, for example, on a relatively inexpensive diamond or other material test piece, in which successive ablations are conducted under differing conditions, e.g., differing Z-axis positions at successive positions in the X-Y plane. After the series of ablations, the test piece is examined to determine the optimal conditions of orientation, e.g., smallest spot size. The conditions of the optimal orientation are then used to determine the focal plane and hence the calibrated reference plane.

The user has complete control over character sizing. Once the cursors are placed on the girdle (according to girdle dimensions) the computer will display a first choice which the user can change.

A motorized Z-axis is provided for focusing the laser onto the workpiece surface. This Z-axis is computer controlled, and enables the operator to focus onto the girdle 12 of the diamond 13 by means of the computer keyboard controls, with direct position input to computerized numeric control (CNC). The girdle profile is determined by reference to an orthogonal view to the girdle surface, and therefore the Z-axis may be controlled for each coordinate. A system may also be provided which uses hand operated micrometer screws for focusing, for example where long inscriptions on fancy shaped stones necessitates the use of segmented inscriptions.

The parameters of the inscription process, including laser power, Q-switch frequency and inscription speed, may be controlled for optimization of the laser-material interaction when switching between substrates and differing surface qualities. Thus, the present invention allows the implementation of varying ablation sequences based on the desired inscription and the characteristics of the workpiece. Often, the characteristics of the workpiece are known and input into the control system, i.e., by a bar code, magnetic strip, manual keying, database retrieval, or other method. However, the system according to the present invention may also include a system for itself determining a characteristic or set of characteristics of the workpiece and implement an inscription process based on the input or determined characteristics and the desired resulting inscription. Likewise, where an inscription is preexisting, the system according to the present invention may analyze the existing inscription and produce a modified inscription. Thus, where features according to the present inscription method are desired, they may be superimposed on or added to existing inscriptions. Further, an old inscription may be analyzed and stored according to the present methods without any modifications thereto, e.g., for security and authentication purposes.

SOFTWARE

The computer controller preferably operates in a Windows environment, although Windows 95 or NT, Macintosh, UNIX derivatives, X-terminal or other operating system which supports the various system components may be employed. The optical feedback system and preview of inscription functions advantageously employ a graphic user interface.

All machine features are generally controlled by the software, with the exception of laser pulse power and pulse frequency, which are set from power supply panel. Of course, the laser control system may be completely automated with a computer control, allowing software control over pulse power, Q-switch frequency, and inscription speed.

User control and input for interaction with the software, which is preferably a graphic user interface system, is generally performed via mouse 161 and keyboard 160. Data entry of workpiece information may employ other input devices, such as a microphone, optical or bar code scanner, gemstone characteristic sensor, magnetic disk or stripe, or other known input devices.

The software can generate various reports according to specifications and formats as desired, based on an individual inscription procedure or a number of inscriptions. The software may also be used to generate a certificate of authenticity with anti-forgery and anti-tamper features, with an image of the workpiece.

Images obtained through the CCD images can be stored, for example, on magnetic disks or optical media, and may be stored locally or remotely. Such storage may be useful in order to identify and inventory workpieces, or to ensure system operation.

The computer may also be provided with standard computer networking and communications systems. For example, an Ethernet communication link, IEEE 802.3 may be used to communicate over a local area network. Communications with a central database may occur over telephone lines using a standard analog modem, e.g., v.34, ISDN, Frame Relay, the Internet (using TCP/IP), or through other types of private networks. Data is preferably encrypted, especially when in transit over unsecure public channels.

Logo and graphic editors are also provided for the creation of logos and graphics. A font editor is provided to edit character raster images of fonts. Because the raster image corresponding to each code is programmable or modifiable, complex symbols may be inscribed with the same ease as letters and numbers, once the symbol is defined as a font character. According to one aspect of the invention, a graphic pictorial image is engraved onto the stone, thereby making the stone an artwork. The pictorial image may be identical or different for each stone, and may also include encoded information. A logo may differ from a character by being larger, with potentially a higher dot density. Thus, characters are generally defined as raster bitmaps, while logos may be further optimized or the laser controlled to obtain a desired appearance.

STONE MOUNT

The mount includes a fixed base, held in fixed position with respect to the frame 140, with a removable holder 118, as shown in FIGS. 7A–7E. The holder 118 can be easily removed or taken out from the fixed base without changing the diamond's orientation. A holder 118 is selected based on the diamond size to be processed in the machine, with various holders available for differing sized stones. The diamond can be easily placed in or removed from the holder and can be externally adjusted to bring the correct part of the girdle to face the camera.

The diamond holder is based on a standard holder known in the diamond industry. The diamond center sits in a concave depression suited to the diamond size. A spring loaded metal strip 110 pushes against the table to hold the diamond securely into the pot 108, while making sure that the table is parallel to the holder 118 axis. If the girdle plane is not parallel to the table or the girdle surface is not parallel to the diamond axis of symmetry, the holder provides two adjustments knobs 105, 117 to correct for those cases so that, when viewed through the video camera 28 on a video screen 159 the girdle 12 is horizontal and the entire relevant surface is in focus. In addition, there are adjustments for rough 106 and precise 104 rotation of the diamond 13 in the holder 118. Rotation about the center axis of the diamond 13 is therefore achieved manually, although an automated or mechanized rotation is also possible. The rough adjustment 106 has 16 rotational steps, while the fine adjustment 104 is continuous.

All of the above adjustments of the diamond in the holder 118 can be performed outside of the inscribing apparatus and the diamond 13 can therefore be pre-aligned before insertion into the machine. The holder 118 is designed in a manner enabling access to all the adjustment knobs with one hand, while the holder 118 is inserted into he machine. Correction through visual on screen feedback 159 can be easily achieved.

The user is provided with a range of controllable-intensity illumination aids. The laser axis, for example, is illuminated with a red LED 20, which is useful for viewing polished girdles 12 in the vertical (Z-axis) camera 28. In order to provide high contrast between the workpiece 11 profile and the background, three groups of LEDs 30 are provided around the microscope objective 10, illuminating the workpiece 11 from three sides. Each side-illumination group 30 may have, e.g., three LEDs. Further, two miniature arc lamps 40 are provided to illuminate the workpiece 11 from the bottom. This lower illumination is useful, e.g., for observing brutted girdles 12 of diamonds 13 in the vertical (Z-axis) camera 28.

The complete holder 118 is very easily inserted into the machine. In the machine there is a fixed base with a slot. The slide 116 of the holder 118 slides in the slot, in the manner of a credit card or cassette tape, and comes to a precise halt. Spring based ball-tipped plungers facilitate the sliding action and prevent the holder from making any movement when the machine is operating, by engaging countersunk recesses 103. The holder 118 can be taken out and inserted back again with the diamond 13 coming to the same place as before.

The general structure of the holder 118 is shown in FIGS. 7A–7E. The operator can hold the unit with one hand, normally the left hand, and insert the holder into the slot. With the same hand the operator can make all the adjustments while monitoring the video screen and operating the mouse or keyboard with his right hand. The holder 18 position in the slot is very well-defined and the holder can be taken out and reinserted with the diamond 13 and holder 118 regaining the same position. When taken out, the holder 118 has an "out" position where it is still supported by the slide 116 and the stone is 40 mm out of the machine. In this position, the stone can be inked, inspected, cleaned, etc., without need for the user to support the unit with one hand.

The stone 11 is positioned by the holder 118 and mount so that the center axis is horizontal and is perpendicular to the laser beam. The holder 118 is made of steel. The contact points are the concave cup 108 which supports the center of the diamond, and a strip 110 which presses on the table toward the cup 108 in a manner that assures parallelism of the table to the symmetry axis of the holder 118, and assures correct positioning with respect to the laser beam. In a preferred arrangement, three sizes of holders 118 are provided to cover a range of diamond 13 sizes. The holder 118 can support any stone which has a center and a table. In addition, holders 118 may also be designed to accommodate special fancy shapes.

In general, it is desired to make the set-up and inscribing times approximately equal, so that the machine is always busy inscribing. Thus, further improvements in set-up time will not improve throughput. Therefore, a set of stone holders is provided. The user is provided with enough holders ready for inscribing, and that means the machine is inscribing almost continuously. The procedure is as follows:

Stones are prealigned on holders. The operator, on completing the inscription, removes the holder with an inscribed stone and inserts a prepared holder with a stone to be inscribed. Minor adjustments may be required of the diamond or the holder, which may be accomplished under guidance of the video imaging system. In addition, the operator must also input or define the inscription. The inscription process is then commenced. During the inscription, the operator can remove the stone from the previously used holder, allowing reuse. Generally, a large number of holders will not be required to ensure that the inscribing system is always busy, i.e., there is always a holder ready when the inscribing operation is complete. Where single operator productivity is maximum, a second operator may assist in mounting stones in holders and/or defining the inscription process.

Mounted stones are held by a holder 119 which has a design which depends on the fact that some of the girdle 12 must be exposed for the inscription process to take place. Thus, the holder 119 is provided with three fine "claws" 120 which can be opened and closed by pressing a "trigger" 112. The claws 120 are spring loaded in the closed position. The claws 120 grasp around the girdle 12 (between prongs of the setting) and press the table against a flat surface 138 upon release of the trigger 112. The flat surface 138 is perpendicular to the gemstone central axis. The holder 119 design thus assures that the gemstone 11 is centered and held firmly, and allows the stone to be rotated to a desired location for an inscription.

Since a mounted stone is held in an opposite manner from an unmounted stone, the inscription direction is preferably reversed. This reversal is accomplished, for example, within the control software. In this case, the inscription may be inverted, with the inscription process commencing from the "beginning", or the inscription made in reverse order. In order to facilitate the following of the inscription process by the human operator, the inscription preferably proceeds from the "beginning", and the reversal is selected as a screen "button" of the graphic user interface system. In addition, the processed video image of the stone may also be selectively inverted, so that the apparent orientation of the stone in a processed image during mounted and unmounted inscription operations is the same.

The operator will always "OK" the process before laser operation. He will either see the complete inscription on the text screen, or on the video directly on the girdle.

When the inscription is completed the operator can judge (even before cleaning) whether the inscription is successful. Even after cleaning, so long as the stone remains seated in the holder, will return to exactly the same position. The operator can choose to repeat the whole inscription or parts thereof any number of times he wishes to. Verification of the inscription is performed prior to removal of the diamond from the holder, so that the process may be repeated if necessary. The inscription is clearly visible on the video screen even before cleaning the ink/graphite from the stone. Even with the preferred 200 times magnification, an inscription will have to be extremely long in order not to be wholly visible on the screen.

Figure 12:
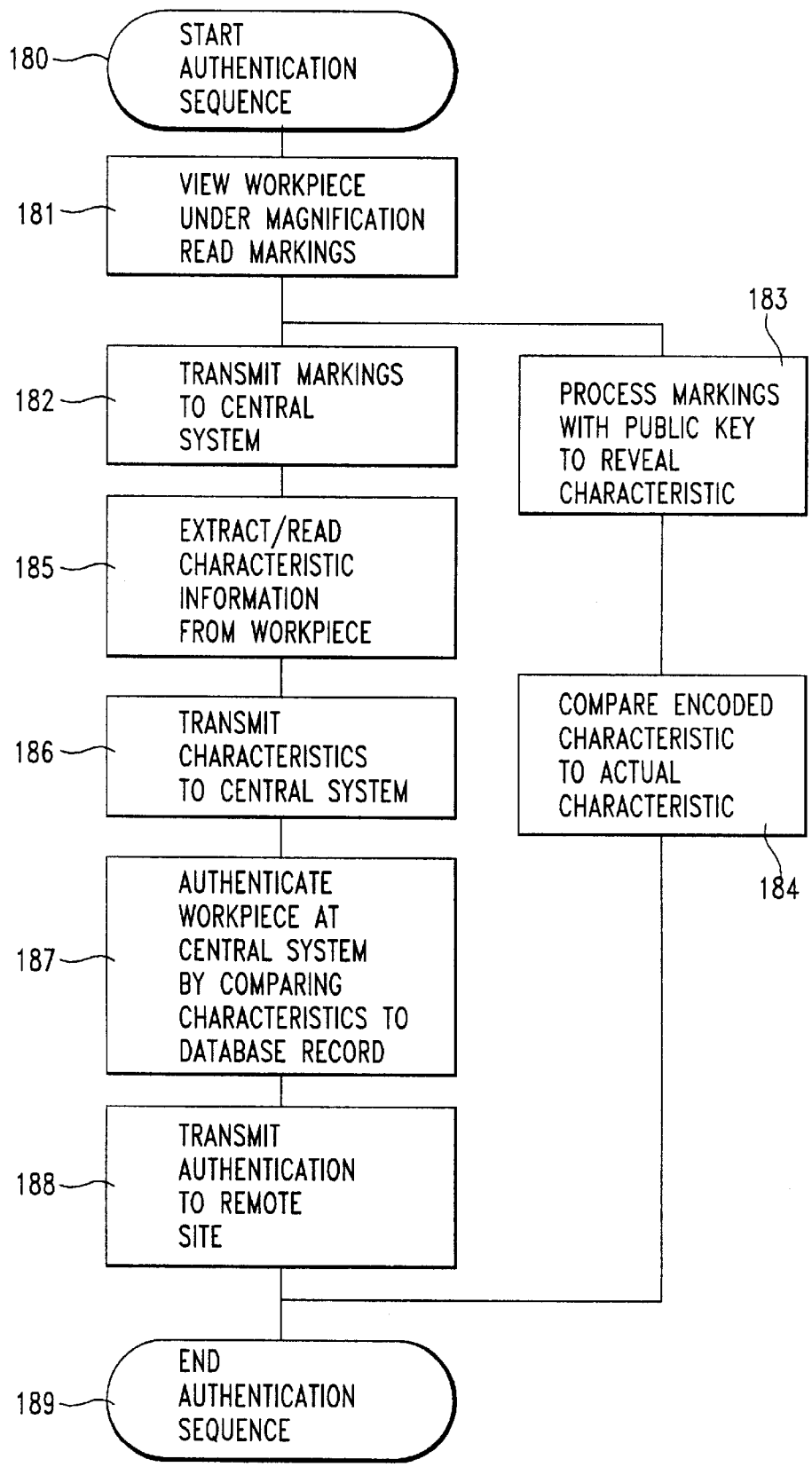
FIG. 12 is a flow chart depicting an authentication sequence according to the present invention.

AUTHENTICATION

Where a workpiece bears a marking, it may be desired to determine whether the marking is authentic, for example according to the flow chart depicted in FIG. 12. The workpiece is viewed under magnification to read markings present thereon 181. The authentication process provides at least two options. First, the markings may be encrypted, and are thus processed with a key 183, e.g., a public key. Where the actual characteristics of the stone form the encrypted message, the decrypted message is compared to the actual characteristics of the workpiece 184. Thus, the authenticity may be determined. Alternately, the markings may include a code which identifies the workpiece, allowing retrieval of information relating to the workpiece from a database. The database thus stores the characterizing information.

In a second embodiment, also shown in FIG. 12, the authentication process involves a remote system. Therefore, the markings are transmitted to a central system 182. The characteristics of the workpiece are read or extracted 185 and also transmitted to the central system 186. The central system then authenticates the marking and the characteristics 187, for example against a stored database of characteristics of marked workpieces. The authentication result is then transmitted to the remote site 189.

ENCRYPTION

Figure 13A:
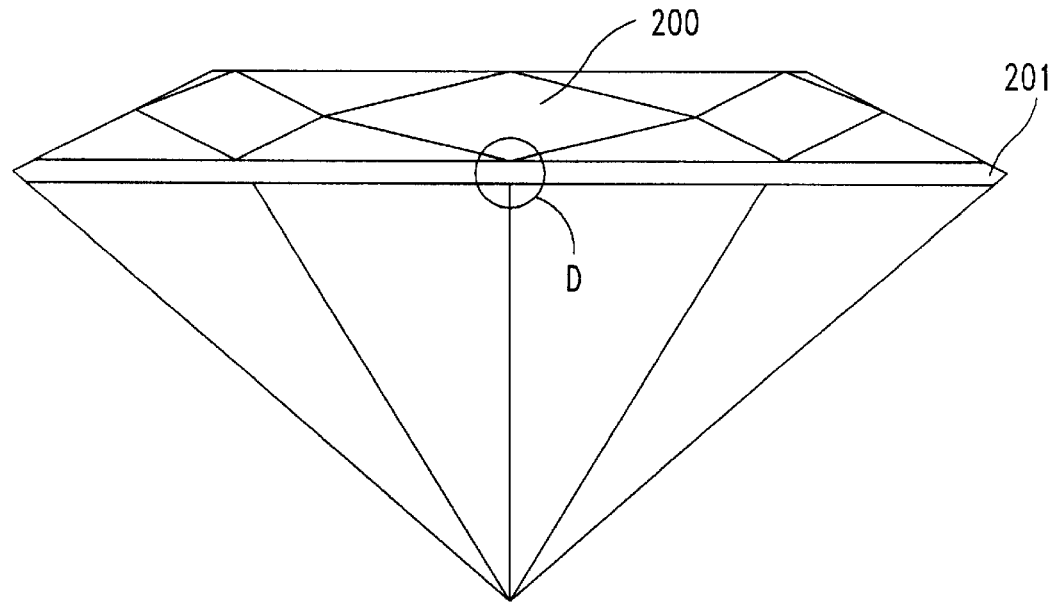
FIGS. 13A, 13B, 13C and 13D show details of a marked diamond, a two dimensional marking pattern, a modulated dot placement encoding scheme, and a detail of the marked diamond, according to the present invention.
Figure 13D:
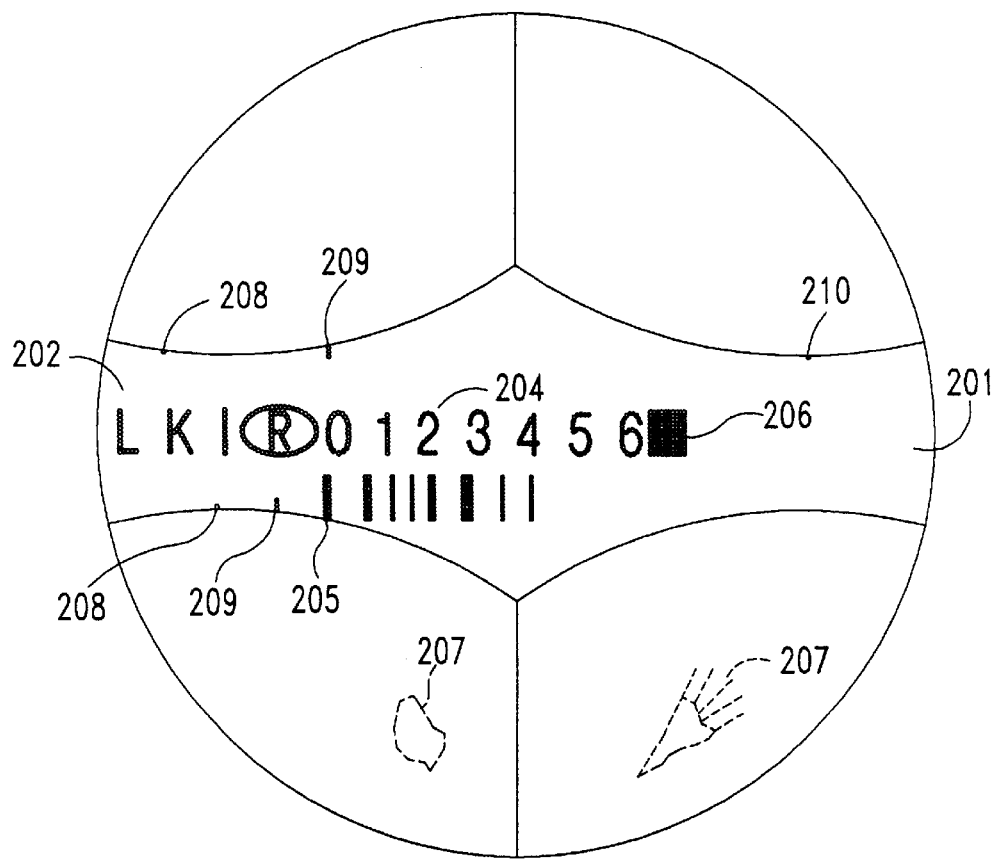

A diamond 200, as shown in FIG. 13A, with further detail, enlarged in FIG. 13D, is provided with a number of identification and security features. The diamond 200, for example, is a color F stone weighing 0.78 Carats, grade VS2 with two identified flaws 207. The diamond 200 has a set of markings inscribed on the girdle 201. The markings include an "LKI" logo 202, formed as characters, a trademark registration symbol 203, a serial number in Arabic numerals 204, a one dimensional bar code 205, a two dimensional code 206, a set of visible dimensional references 209, and single ablation spots 208, 210 having defined locations. For most purposes, the logo identifies the series of marking, while the serial number is used to identify the diamond 200. In order to encode further information, a visible bar code 205 allows, for example, binary information to be encoded and retrieved from the diamond 200. The two dimensional code generally requires a machine for reading, and allows high density data encoding. The visible dimensional references 209 allow use of a reticle to measure distances, providing additional characteristics of the diamond 200 which may be used to uniquely define the diamond 200. The single ablation spots 208, 210 are less visible, and may thus require a key for searching. In other words, authentication of these spots may require transmission of their location, with confirmation by inspection of the diamond 200. The marking 210, for example, has a defined physical relation to one or both flaws 207, making copying very difficult.

Figure 13B:
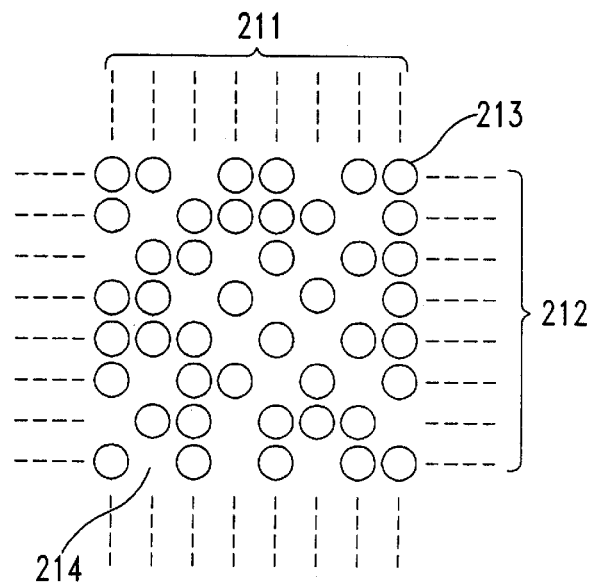
Figure 13C:
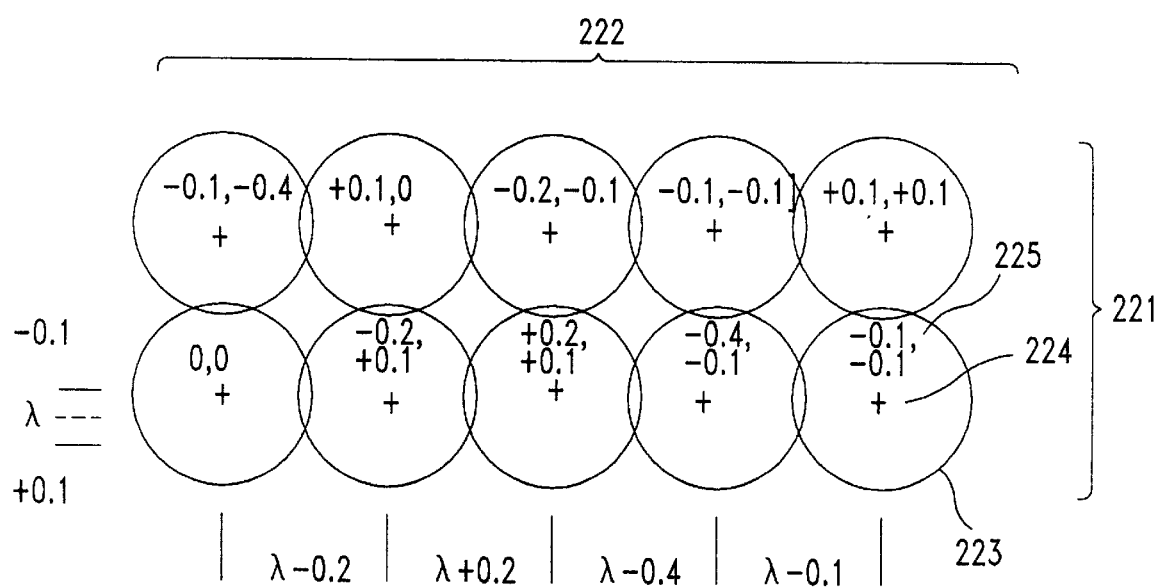
Figure 14:
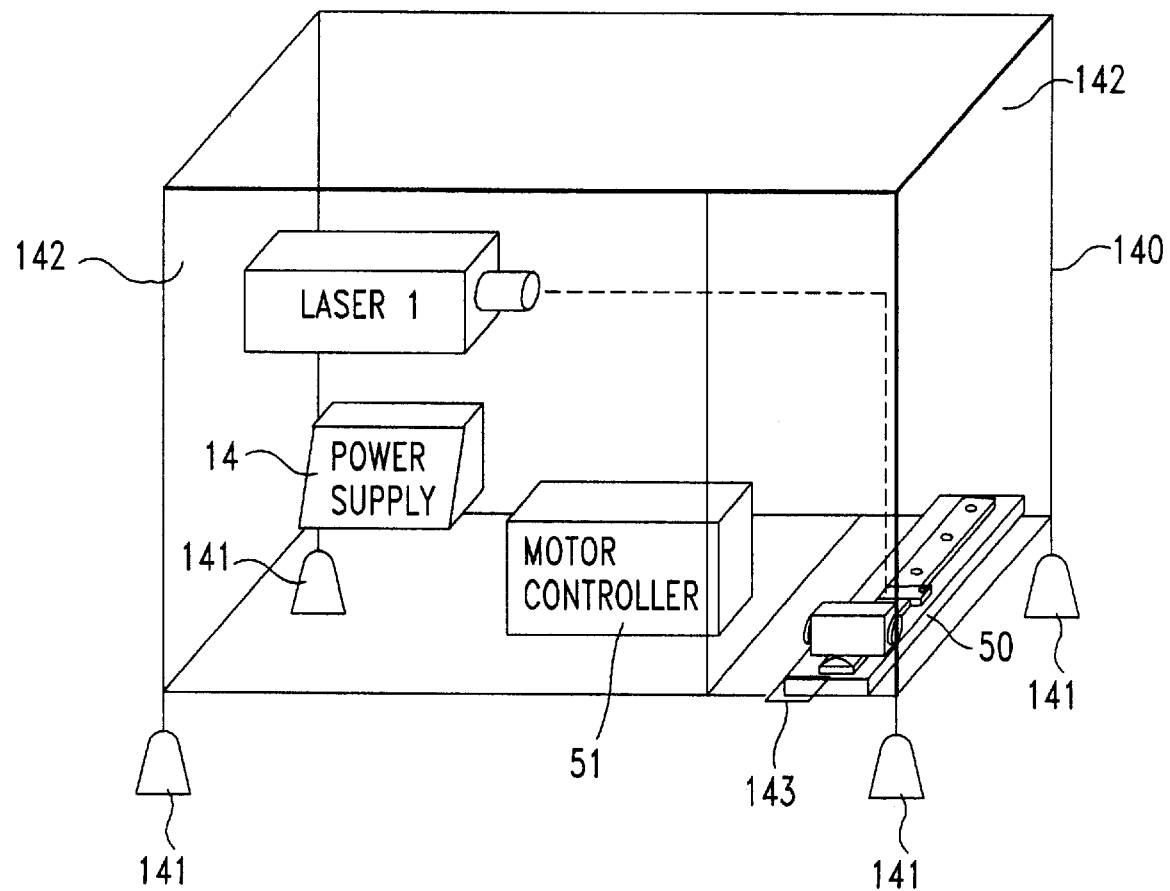
FIG. 14 is a semischematic view of the mounting frame, showing vibration dampers the corners thereof.

FIG. 13B shows, in more detail, a typical two dimensional code, with simple binary modulation. Thus, the presence 213 or absence 214 of an ablation at a coordinate 211, 212 location defines the data pattern. On the other hand, FIG. 13C shows a more complex code. In this case, ablations are spaced discontinuously or partially overlapping, so that an outline or partial outline of each spot 223 may be identified. Due to stochastic processes, the actual placement of the center 224 of an ablation, or its outline may vary. However, the modulation pattern imposed may be greater in amplitude than the noise, or a differential encoding technique employed so that the noise is compensated. Thus, an array of spots 223 on generally coordinate 221, 222 positions, with the exact positions 225 modulated according to a pattern 225. In this case, without knowledge of the modulation scheme, it would be difficult to read the code, thus making it difficult to copy the code. Further, to the extent that the noise amplitude is near the apparent signal amplitude, a copying system may require very high precision.

There has thus been shown and described novel receptacles and novel aspects of laser workpiece marking systems and related databases, which fulfill all the objects and advantages sought therefor. Many changes, modifications, variations, combinations, subcombinations and other uses and applications of the subject invention will, however, become apparent to those skilled in the art after considering this specification and the accompanying drawings which disclose the preferred embodiments thereof All such changes, modifications, variations and other uses and applications which do not depart from the spirit and scope of the invention are deemed to be covered by the invention, which is to be limited only by the claims which follow.

What is claimed is:

1. A laser energy microinscribing system, comprising:

a pulse laser energy source;

a workpiece mounting system, allowing optical access to a mounted workpiece;

an optical system for focusing laser energy from the laser energy source, onto the workpiece;

means for directing said focused laser energy onto a desired portion of the workpiece, having a control input;

an imaging system for viewing the workpiece from a plurality of vantage points and obtaining image information from the workpiece;

an input for receiving marking instructions;

a processor for controlling said directing means based on said marking instructions and said imaging system, to selectively generate a marking based on said instructions and a predetermined program; and a storage system, coupled to said imaging system, for storing said information relating to images of a plurality of workpieces.

2. The laser energy microinscribing system according to claim 1, wherein said pulse laser energy source comprises a semiconductor diode excited Q-switched neodynium laser.

3. The laser energy microinscribing system according to claim 2, wherein said laser is a Nd:YLF laser with an internal harmonic converter having an output at 530 nm.

4. The laser energy microinscribing system according to claim 1, further comprising a power supply for said pulse laser energy source.

5. The laser energy microinscribing system according to claim 1, further comprising a chassis for rigidly supporting said pulse laser energy source, said workpiece mounting system, said optical system, and said directing means.

6. The laser energy microinscribing system according to claim 1, further comprising a power supply for said pulse laser energy source and a chassis for rigidly supporting said pulse laser energy source, said workpiece mounting system, said optical system, said directing means and said power supply.

7. The laser energy microinscribing system according to claim 1, further comprising a chassis for rigidly supporting said pulse laser energy source, said workpiece mounting system, said optical system, and said directing means, said directing means repositioning the workpiece with respect to said chassis.

8. The laser energy microinscribing system according to claim 1, wherein said workpiece mounting system comprises a fixed member, detachable member and a mounting clamp for fixing the workpiece to said detachable member.

9. The laser energy microinscribing system according to claim 1, wherein the workpiece is a gemstone.

10. The laser energy microinscribing system according to claim 1, wherein the workpiece is a cut diamond.

11. The laser energy microinscribing system according to claim 1, wherein said optical system comprises a beam expander, a dichroic mirror and a focusing lens.

12. The laser energy microinscribing system according to claim 1, wherein said directing means comprises a translatable stage having at least three axes of movement.

13. The laser energy microinscribing system according to claim 1, wherein said directing means is controlled to produce a set of partially overlapping irradiated areas from said pulse laser energy source.

14. The laser energy microinscribing system according to claim 1, wherein said directing means is controlled to produce a set of continuous shapes formed of partially overlapping irradiated areas from said pulse laser energy source.

15. The laser energy microinscribing system according to claim 1, wherein said directing means is controlled to be at rest during a laser pulse of said pulse laser energy source.

16. The laser energy microinscribing system according to claim 1, wherein said imaging system comprises an optical path including at least a portion of the workpiece and being coaxial with at least a portion of an axis of a laser pulse of said pulse laser energy source incident on the workpiece.

17. The laser energy microinscribing system according to claim 1, wherein said imaging system comprises an optical path including at least a portion of the workpiece and being perpendicular to at least a portion of an axis of a laser pulse of said pulse laser energy source incident on the workpiece.

18. The laser energy microinscribing system according to claim 1, wherein said imaging system comprises a first optical path including at least a portion of the workpiece and being coaxial with at least a portion of an axis of a laser pulse of said pulse laser energy source incident on the workpiece and a second optical path including said portion of the workpiece and being perpendicular to said axis of said laser pulse.

19. The laser energy microinscribing system according to claim 1, wherein said imaging system comprises an electronic imaging device for transmitting image information to said processor, said processor controlling said directing means further based on said image information.

20. The laser energy microinscribing system according to claim 1, wherein said imaging system images a portion of the workpiece on which an output of said pulse laser energy source is incident through a dichroic mirror.

21. The laser energy microinscribing system according to claim 1, wherein said input for receiving marking instructions comprises a bar code reader.

22. The laser energy microinscribing system according to claim 1, wherein said input for receiving marking instructions comprises an optical image transducer.

23. The laser energy microinscribing system according to claim 1, wherein said input for receiving marking instructions comprises an input for receiving information relating to a quality of the workpiece.

24. The laser energy microinscribing system according to claim 1, wherein said input for receiving marking instructions comprises an sensor for automatically determining a characteristic of the workpiece.

25. The laser energy microinscribing system according to claim 1, further comprising a telecommunications link, wherein said storage system comprises a remote electronic database.

26. The laser energy microinscribing system according to claim 1, wherein said processor analyzes said marking instructions and said stored information and selectively controls said directing means based on said analysis.

27. The laser energy microinscribing system according to claim 1, wherein said storage system stores information relating to images of workpieces in conjunction with information relating to said marking instructions.

28. The laser energy microinscribing system according to claim 1, further comprising an input for receiving information relating to an image of a workpiece and means for comparing to determine a relation between said information relating to the workpiece and said stored information.

29. The laser energy microinscribing system according to claim 28, further comprising an output indicative of a relation between the workpiece and said stored information.

30. The laser energy microinscribing system according to claim 28, wherein said input receives information from said imaging system.

31. The laser energy microinscribing system according to claim 1, receiving information from said imaging system relating to an image of the workpiece, further comprising means for comparing said received information and said marking instructions with said stored information, to determine a correspondence of the workpiece marked in accordance with said marking instructions with any stored information.

32. The laser energy microinscribing system according to claim 1, further comprising means for comparing said marking instructions with said stored information, to determine a correspondence of a resulting workpiece marked in accordance with said marking instructions with any stored information.

33. A laser energy microinscribing system, comprising:
- a semiconductor excited Q-switched solid state laser energy source;
- a cut gemstone mounting system, allowing optical access to a mounted workpiece;
- an optical system for focusing laser energy from the laser energy source onto a cut gemstone;
- a displaceable stage for moving said gemstone mounting system with respect to said optical system so that said focused laser energy is presented to desired positions on said gemstone, having a control input;
- an imaging system for viewing the gemstone from a plurality of vantage points;
- a rigid frame supporting said laser, said optical system and said stage in fixed relation, to resist differential movements of said laser, said optical system and said stage and increase immunity to vibrational misalignments;
- an input for receiving marking instructions;
- a processor for controlling said displaceable stage based on said marking instructions and said imaging system, to selectively generate a marking based on said instructions and a predetermined program; and
- a storage system, coupled to said imaging system, for electronically storing information relating to images of a plurality of workpieces.

34. A method of microinscribing a workpiece with laser energy from a pulse laser energy source, focused by an optical system on the workpiece, comprising the steps of:
- mounting a workpiece in a mounting system;
- directing the focused laser energy onto a desired portion of the workpiece;
- imaging the workpiece from a plurality of vantage points;
- receiving marking instructions as at least one input;
- controlling the directing of the focused laser energy based on the marking instructions and the imaging, to selectively generate a marking based on said instructions; and
- storing information relating to images of a plurality of workpieces.

35. The method according to claim 34, wherein the pulse laser energy source comprises a semiconductor diode excited Q-switched neodynium laser.

36. The method according to claim 35, wherein the laser is a Nd:YLF laser having a internal harmonic converter and an output of about 530 nm.

37. The method according to claim 34, wherein the system further comprises a chassis for rigidly supporting the pulse laser energy source, the mounting system, the optical system, and a focused laser energy directing system, further comprising the step of repositioning the workpiece with respect to the chassis.

38. The method according to claim 34, wherein the mounting system comprises a fixed member, a detachable member and a mounting clamp for fixing the workpiece to the detachable member, further comprising the step of rigidly linking the detachable member to the fixed member.

39. The method according to claim 34, wherein the workpiece is a gemstone.

40. The method according to claim 34, wherein the workpiece is a cut diamond.

41. The method according to claim 34, wherein the optical system comprises a beam expander, a dichroic mirror and a focusing lens, further comprising the step of expanding an output of the pulse laser energy source with the beam expander, selectively reflecting at least a portion of the expanded beam with the dichroic mirror, and focusing the reflected expanded beam on the workpiece with the focusing lens.

42. The method according to claim 34, wherein the optical system comprises a beam expander, a dichroic mirror and a focusing lens, further comprising the step of expanding an output of the pulse laser energy source with the beam expander, selectively reflecting at least a portion of the expanded beam with the dichroic mirror, focusing the reflected expanded beam on the workpiece with the focusing lens and electronically imaging the workpiece through the dichroic mirror.

43. The method according to claim 34, further comprising the step of electronically imaging a portion of the workpiece on which an output of the pulse laser energy source is incident through a dichroic mirror.

44. The method according to claim 34, wherein said controlling the directing step comprises controlling movement of a translatable stage along at least three axes.

45. The method according to claim 34, wherein said controlling the directing step comprises generating a set of partially overlapping irradiated areas from the pulse laser energy source.

46. The method according to claim 34, further comprising the step of fixing a position of the workpiece with respect to a focal point of the pulse laser energy source during a laser pulse.

47. The method according to claim 34, wherein said imaging step comprises imaging through an optical path including at least a portion of the workpiece and being coaxial with at least a portion of an axis of a laser pulse of the pulse laser energy source incident on the workpiece.

48. The method according to claim 34, wherein said imaging step comprises imaging through an optical path including at least a portion of the workpiece and being perpendicular to at least a portion of an axis of a laser pulse of the pulse laser energy source incident on the workpiece.

49. The method according to claim 34, wherein said imaging step comprises imaging through a first optical path including at least a portion of the workpiece and being coaxial with at least a portion of an axis of a laser pulse of said pulse laser energy source incident on said workpiece and a second optical path including said portion of the workpiece and being perpendicular to said axis of said laser pulse.

50. The method according to claim 34, further comprising the steps of transmitting electronic image information to said processor, and controlling the directing further based on the image information.

51. The method according to claim 34, further comprising the step of receiving marking instructions from a bar code reader.

52. The method according to claim 34, further comprising the step of receiving marking instructions from an optical image transducer.

53. The method according to claim 34, further comprising the step of marking the workpiece with information relating to a quality of the workpiece.

54. The method according to claim 34, further comprising the steps of automatically determining a characteristic of the workpiece and using the determined characteristic for marking instructions.

55. The method according to claim 34, further comprising the step of communicating information relating to images through a telecommunications link and storing the information in a remote electronic storage database.

56. The method according to claim 34, further comprising the step of deriving the stored information from the imaging.

57. The method according to claim 34, further comprising the step of storing information relating to images of workpieces in conjunction with information relating to the marking instructions.

58. The method according to claim 34, further comprising the steps of receiving information relating to an image and determining a relation between the workpiece and the stored information.

59. The method according to claim 34, further comprising the steps of receiving information relating to an image of a workpiece, and producing an output indicative of a relation between the workpiece and said stored information.

60. The method according to claim 34, further comprising the step of comparing images received during said imaging step with previously stored information.

61. The method according to claim 34, further comprising the steps of receiving information relating to an image of the workpiece, comparing the received information and the marking instructions with previously stored information, to determine a correspondence of the workpiece marked in accordance with the marking instructions with any stored information.

62. The method according to claim 34, further comprising the steps of comparing the marking instructions with previously stored information, to determine a correspondence of a resulting workpiece marked in accordance with the marking instructions with any stored information.

63. The method according to claim 34, further comprising the steps of analyzing the marking instructions and previously stored information and selectively controlling the marking based on said analysis.

64. The method according to claim 34, wherein said marking comprises a set of lines or spots.

65. The method according to claim 34, further comprising the steps of:
   determining a characteristic of the workpiece;
   encrypting an expression of the determined characteristic of the workpiece;
   providing the encrypted expression as a received input;
   storing information relating to the characteristic; and
   authenticating the workpiece based on a description of the marking on a workpiece and a determined characteristic of the workpiece.

66. The method according to claim 34, further comprising the steps of identifying a landmark of the workpiece from images obtained during the imaging step; microinscribing a marking at a position based on a position of the identified landmark; and storing the position.

67. The method according to claim 34, wherein at least one received input comprises encrypted information.

68. The method according to claim 34, further comprising the steps of extracting information from an image of the workpiece, encrypting the extracted information, and providing the encrypted information as a received input.

69. The method according to claim 34, further comprising the steps of determining a characteristic of the workpiece, encrypting an expression of the determined characteristic of the workpiece using a public key-private key encryption algorithm, and providing the encrypted expression as a received input.

70. The method according to claim 69, further comprising the steps of decrypting the marking using a public key and comparing the decrypted expression with a characteristic of the workpiece, to authenticate the marking.

71. A laser energy microinscribing system, comprising:
   a semiconductor excited Q-switched solid state laser energy source;
   a cut gemstone mounting system, allowing optical access to a mounted workpiece;
   an optical system for focusing laser energy from the laser energy source onto a cut gemstone;
   a displaceable stage for moving said gemstone mounting system with respect to said optical system so that said focused laser energy is presented to desired positions on said gemstone, having a control input;
   an imaging system for viewing the gemstone from a plurality of vantage points; and
   a rigid frame supporting said laser, said optical system and said stage in fixed relation, to resist differential movements of said laser, said optical system and said stage and increase immunity to vibrational misalignments.

72. The laser energy microinscribing system according to claim 71, wherein said imaging system images a portion of the workpiece on which an output of said laser energy source is incident, through a dichroic mirror.

73. The laser energy microinscribing system according to claim 71, further comprising means for automatically determining a characteristic of the workpiece.

74. The laser energy microinscribing system according to claim 71, wherein said laser energy source comprises a semiconductor diode excited Q-switched Nd:YLF laser with a harmonic converter having an output of about 530 nm.

75. The laser energy microinscribing system according to claim 71, wherein said imaging system comprises a first optical path including at least a portion of the workpiece and being coaxial with at least a portion of an axis of a laser pulse of said laser energy source incident on the workpiece and a second optical path including said portion of the workpiece and being perpendicular to said axis of said laser pulse.

76. The laser energy microinscribing system according to claim 71, further comprising a power supply for said pulse laser energy source.

77. The laser energy microinscribing system according to claim 71, further comprising a chassis for rigidly supporting said laser energy source, said workpiece mounting system, said optical system, and said translatable stage.

78. The laser energy microinscribing system according to claim 71, further comprising a power supply for said laser energy source and a chassis for rigidly supporting said laser energy source, said workpiece mounting system, said optical system, said translatable stage and said power supply.

79. The laser energy microinscribing system according to claim 71, further comprising a chassis for rigidly supporting said laser energy source, said workpiece mounting system, said optical system, and said translatable stage, said translatable stage repositioning the workpiece with respect to said chassis.

80. The laser energy microinscribing system according to claim 71, wherein said workpiece mounting system comprises a fixed member, detachable member and a mounting clamp for fixing the workpiece to said detachable member.

81. The laser energy microinscribing system according to claim 71, wherein the workpiece is a gemstone.

82. The laser energy microinscribing system according to claim 71, wherein the workpiece is a cut diamond.

83. The laser energy microinscribing system according to claim 71, wherein said optical system comprises a beam expander, a dichroic mirror and a focusing lens.

84. The laser energy microinscribing system according to claim 71, wherein said translatable stage has at least three axes of movement.

85. The laser energy microinscribing system according to claim 71, wherein said translatable stage is controlled to produce a set of partially overlapping irradiated areas from said laser energy source.

86. The laser energy microinscribing system according to claim 71, wherein said translatable stage is controlled to be at rest during a laser pulse of said laser energy source.

87. The laser energy microinscribing system according to claim 71, wherein said imaging system comprises an optical path including at least a portion of the workpiece and being coaxial with at least a portion of an axis of a laser pulse of said laser energy source incident on the workpiece.

88. The laser energy microinscribing system according to claim 71, wherein said imaging system comprises an optical path including at least a portion of the workpiece and being perpendicular to at least a portion of an axis of a laser pulse of said laser energy source incident on the workpiece.

\* \* \* \* \*